United States Patent
Krappmann et al.

(10) Patent No.: US 10,502,741 B2
(45) Date of Patent: Dec. 10, 2019

(54) MEANS AND METHODS FOR DETECTING ACTIVATED MALT1

(71) Applicants: Helmholtz Zentrum München Deutsches Forschungszentrum für Gesundheit und Umwelt (GmbH), Neuherberg (DE); Technische Universität München, München (DE)

(72) Inventors: Daniel Krappmann, München (DE); Andrea Eitelhuber, München (DE); Steven Verhelst, Essen (DE)

(73) Assignees: Helmholtz Zentrum München Deutsches Forschungszentrum für Gesundheit und Umweld (GmbH), Neuherberg (DE); Technische Universität München, München (DE)

( * ) Notice: Subject to any disclaimer, the term of this patent is extended or adjusted under 35 U.S.C. 154(b) by 99 days.

(21) Appl. No.: 15/108,655

(22) PCT Filed: Jan. 20, 2015

(86) PCT No.: PCT/EP2015/050951
§ 371 (c)(1),
(2) Date: Jun. 28, 2016

(87) PCT Pub. No.: WO2015/110406
PCT Pub. Date: Jul. 30, 2015

(65) Prior Publication Data
US 2016/0327558 A1 Nov. 10, 2016

(30) Foreign Application Priority Data
Jan. 21, 2014 (EP) .................................. 14151913

(51) Int. Cl.
*G01N 33/53* (2006.01)
*G01N 33/573* (2006.01)
*G01N 33/532* (2006.01)
*C12N 9/64* (2006.01)

(52) U.S. Cl.
CPC ......... *G01N 33/573* (2013.01); *C12N 9/6472* (2013.01); *G01N 33/532* (2013.01); *C07K 2319/43* (2013.01); *C07K 2319/60* (2013.01); *G01N 2333/96466* (2013.01); *G01N 2800/00* (2013.01); *G01N 2800/52* (2013.01)

(58) Field of Classification Search
CPC ............... G01N 33/573; G01N 33/532; G01N 2800/52; G01N 2800/00; G01N 2333/96466; C12N 9/6472; C07K 2319/43; C07K 2319/60
See application file for complete search history.

(56) References Cited

U.S. PATENT DOCUMENTS

2010/0184709 A1* 7/2010 Thome ..................... C12Q 1/37
514/20.1

FOREIGN PATENT DOCUMENTS

WO WO-2008/146259 A2 12/2008
WO WO-2011/157222 A1 12/2011

OTHER PUBLICATIONS

Hachmann et al (Biochem. J. (2012) 443, 287-295).*
Saunders et al., (Analytical Biochemistry 2000;vol. 284, 114-124).*
Santa Cruz MALT1 Antibody (2007, retrieved from https://www.scbt.com/scbt/browse/malt1-Antibodies/_/N-51ww2g).*
Kato et al (Nature Chem.Biol. 2005;vol. 1 No. 1, 33-38).*
Ueki et al (Tetrahedron Letters 1987;28(52),6617-20).*
Fontan, L. et al., MALT1 Small Molecule Inhibitors Specifically Suppress ABC-DLBCL In Vitro and In Vivo, Cancer Cell, 22: 812-824 (2012).
Hachmann, J. et al., Mechanism and specificity of the human paracaspase MALT1, Biochemical Journal, 443: 287-295 (2012).
International Search Report for PCT/EP2015/050951, 7 pages (dated May 20, 2015).
Krappman, D., Attacking MALT1 for ABD-DLBCL therapy, Oncotarget, 3(12): 1489-1490 (2012).
Written Opinion for PCT/EP2015/050951, 7 pages (dated May 20, 2015).

* cited by examiner

*Primary Examiner* — Julie Wu
*Assistant Examiner* — Carmencita M Belei
(74) *Attorney, Agent, or Firm* — Brenda H. Jarrell; Choate Hall & Stewart LLP

(57) ABSTRACT

The present invention provides means and methods for selectively detecting activated MALT1 in a sample. Moreover, the present invention provides a method for diagnosing diseases, which are characterized by an increased MALT1 activity. Finally, the present invention provides methods for identifying patients which are amenable to treatment with a therapeutic agent capable of inhibiting MALT1 activity.

16 Claims, 11 Drawing Sheets
Specification includes a Sequence Listing.

SEQUENCE LISTING

<160> NUMBER OF SEQ ID NOS: 13

<210> SEQ ID NO 1
<211> LENGTH: 5046
<212> TYPE: DNA
<213> ORGANISM: human

<400> SEQUENCE: 1

```
cgaggctccg tgccccgccc cccgggtgcc ccgccccttt gcgcggctgg cgcggccagc      60
aggccaggct cccctcggca aacctgtcta attggggcgg ggagcggagc ttcctcctct     120
gagggccgtg ccgcgctgcc agatttgttc ttccgcccct gcctccgcgg ctcggaggcg     180
agcggaaggt gccccggggc cgaggccgt gacggggcgg gcgggagccc cggcagtccg      240
gggtcgccgg cgagggccat gtcgctgttg ggggaccccg tacaggccct gccgccctcg     300
gccgccccca cggggccgct gctcgcccct ccggccggcg cgaccctcaa ccgcctgcgg     360
gagccgctgc tgcggaggct cagcgagctc ctggatcagg cgcccgaggg ccggggctgg     420
aggagactgg cggagctggc ggggagtcgc gggcgcctcc gcctcagttg cctagacctg     480
gagcagtgtt ctcttaaggt actggagcct gaaggaagcc ccagcctgtg tctgctgaag     540
ttaatgggtg aaaaaggttg cacagtcaca gaattgagtg atttcctgca ggctatggaa     600
cacactgaag ttcttcagct tctcagcccc ccaggaataa agattactgt aaacccagag     660
tcaaaggcag tcttggctgg acagtttgtg aaactgtgtt gccgggcaac tggacatcct     720
tttgttcaat atcagtggtt caaaatgaat aaagagattc caaatggaaa tacatcagag     780
cttatttttta atgcagtgca tgtaaaagat gcaggctttt atgtctgtcg agttaataac     840
aatttcacct ttgaattcag ccagtggtca cagctggatg tttgcgacat cccagagagc     900
ttccagagaa gtgttgatgg cgtctctgaa tccaagttgc aaatctgtgt tgaaccaact     960
tcccaaaagc tgatgccagg cagcacattg gttttacagt gtgttgctgt tggaagccct    1020
attcctcact accagtggtt caaaaatgaa ttaccattaa cacatgagac caaaaagcta    1080
tacatggtgc cttatgtgga tttggaacac caaggaacct actggtgtca tgtatataat    1140
gatcgagaca gtcaagatag caagaaggta gaaatcatca taggaagaac agatgaggca    1200
gtggagtgca ctgaagatga attaaataat cttggtcatc ctgataataa agagcaaaca    1260
actgaccagc ctttggcgaa ggacaaggtt gcccttttga taggaaatat gaattaccgg    1320
gagcacccca agctcaaagc tcctttggtg gatgtgtacg aattgactaa cttactgaga    1380
cagctggact tcaaagtggt ttcactgttg gatcttactg aatatgagat gcgtaatgct    1440
gtggatgagt ttttactcct tttagacaag ggagtatatg ggttattata ttatgcagga    1500
catggttatg aaaattttgg gaacagcttc atggtccccg ttgatgctcc aaatccatat    1560
aggtctgaaa attgtctgtg tgtacaaaat atactgaaat tgatgcaaga aaaagaaact    1620
ggacttaatg tgttcttatt ggatatgtgt aggaaaagaa atgactacga tgataccatt    1680
ccaatcttgg atgcactaaa agtcaccgcc aatattgtgt ttggatatgc cacgtgtcaa    1740
ggagcagaag cttttgaaat ccagcattct ggattggcaa atggaatctt tatgaaattt    1800
ttaaaagaca gattattaga agataagaaa atcactgtgt tactggatga agttgcagaa    1860
```

-continued

```
gatatgggta agtgtcacct taccaaaggc aaacaggctc tagagattcg aagtagttta      1920
tctgagaaga gagcacttac tgatccaata cagggaacag aatattctgc tgaatctctt      1980
gtgcggaatc tacagtgggc caaggctcat gaacttccag aaagtatgtg tcttaagttt      2040
gactgtggtg ttcagattca attaggattt gcagctgagt tttccaatgt catgatcatc      2100
tatacaagta tagtttacaa accaccggag ataataatgt gtgatgccta cgttactgat      2160
tttccacttg atctagatat tgatccaaaa gatgcaaata aaggcacacc tgaagaaact      2220
ggcagctact tggtatcaaa ggatcttccc aagcattgcc tctataccag actcagttca      2280
ctgcaaaaat taaggaaca tctagtcttc acagtatgtt tatcatatca gtactcagga      2340
ttggaagata ctgtagagga caagcaggaa gtgaatgttg gaaacctct cattgctaaa      2400 ttagacatgc atcgaggttt gggaaggaag acttgctttc aaacttgtct tatgtctaat      2460
ggtccttacc agagttctgc agccacctca ggaggagcag ggcattatca ctcattgcaa      2520
gacccattcc atggtgttta ccattcacat cctggtaatc caagtaatgt tacaccagca      2580
gatagctgtc attgcagccg gactccagat gcatttattt caagtttcgc tcaccatgct      2640
tcatgtcatt ttagtagaag taatgtgcca gtagagacaa ctgatgaaat accatttagt      2700
ttctctgaca ggctcagaat ttctgaaaaa tgacctcctt gttttgaaa gttagcataa       2760 ttttagatgc ctgtgaaata gtactgcact tacataaagt gagacattgt gaaaaggcaa      2820
atttgtatat gtagagaaag aatagtagta actgtttcat agcaaacttc aggactttga      2880
gatgttgaaa ttacattatt taattacaga cttcctcttt ctaagatttt gtgaattggt      2940
tgaatagttc tatacaaatg aagtatggag gtgtgtatgt ttatatgtat ataacaaat      3000 attttcattg tgaccactct gaagtaagag caatgggaat ggcattattg tagaataagt      3060
cattgtattt ttaacaccag aaagaacctt gccgatcacc aggcataacc taattttatc      3120
catggaagaa acacagaaag gcatctaagt tagagctggc accagaactg agacctccag      3180
aaatctattc cagtattttt tccactacac aactgccttc ctgacaggtt ctgagataag      3240
tgttatgttt gtagatagag tgaaatatat ttatatatat ataaatatat acagatacat      3300
atctgtgtat tatctcaagg aatgtacaaa ctttagtttt tgattataag gacttcactg      3360
caagttttag ttaagaggtt tgtatataaa tctgttatag aacaggctga aatttcttgt      3420
tcataagatt atgaaaccac atgagaagtg ataaaatgtt tgttaaagct agatagaggt      3480
taagaatcaa gatataatgg ataattttca tagctgccta tcagaatttc ccaaatatt       3540 agcatcttcc ttgataatat gtattttctt cttgaatttc actggcctaa tgagataata      3600
ctcttatctt tggctctacc taaaagttgg ttaaaaatgc aattggcatt aacaaggaaa      3660
aatactgaat tagtaatttt aaaagtctca caaagaaaat cccaggccta gatggctgca      3720 tgttgaatt ctgccaaaca ttaaaattag cactaatttt ttgcacactg tttctaaaag       3780
taggagagga aagaacactt cccaacttac tctaggtcag tattaccctg atactagact      3840
agacatcaca agaaaactat aagccaatat tccttattaa tacaaacaca aaaatcatta      3900
acaaaaatat tagcaaactg aatccagcaa cctataaaaa ggattctata tcatgaccaa      3960
gtggaattta tcccaggaat tcaaggttgg ttcaacatct aaaaatcaaa taagctaata      4020
tacagtcagt tctcattatt cacagtaatt atgttctaca gaatattctc ccataaacac      4080
tgaattaaat atggaacaac tgcttttagg agaaagtgta tttgtgtata tgtgtgtata      4140
catatgttta tctcacacac attatgagct tgaattctta attcatccta gcaaattcta      4200
ccttatttta cagaagtgaa agtgaggtat cagaagtgtt aagtgacatg cctgaggcac      4260
```

```
ccccctaaca ggtgtcagag ctgaaattca aaccccatcc agctggcccc ggagccagag    4320
cttcttgtac tacacagaat tgcccctgcc atttccaccc tccagtcatt tctctatgag    4380
actgaagcag gaaggcagag catcatcttg ttcagcctca gctgggaaca tgtgtactgg    4440
gtgactcaaa tttttcaccc atttacacat atccacaaat gactgcaaaa gtgccacgga    4500
tatcaatttg agggttataa attttagcaa gttggtaaat tcacaaatac ataaccttga    4560
ataatgagga tcaactgtac catatttaat aaagcacaaa acccacacag attgtcttat    4620
tacagcattt gataaaatcc aaaactcttt cataaaaaca ctcaacaaac ttaggaataa    4680
aaggaatctt cctagatatg ataaatataa catctatgaa aagcccacac ctaacattat    4740
acttcatggt gatagactga aggctgaatg ttttcccctt aagattggga agaaggacaa    4800
ggatgttcac tcggcactac ttctattcag cattgtactt gaagttctag ccacagcagt    4860
taggttagga attcaaggtt tgttcaacat ctaaaaatca aataagctaa taagaaaag     4920 aggtttatac tgcaaaagaa gtgaaactat atgtattcac agttgataca tagttgtata    4980
tagaaaatgc taaagaatcc ataaaagta ataaatgagt tcaacaggtt aaaaaaaaa    5040 aaaaaa                                                              5046

<210> SEQ ID NO 2
<211> LENGTH: 824
<212> TYPE: PRT
<213> ORGANISM: human

<400> SEQUENCE: 2

Met Ser Leu Leu Gly Asp Pro Leu Gln Ala Leu Pro Pro Ser Ala Ala
1               5                   10                  15

Pro Thr Gly Pro Leu Leu Ala Pro Pro Ala Gly Ala Thr Leu Asn Arg
            20                  25                  30

Leu Arg Glu Pro Leu Leu Arg Arg Leu Ser Glu Leu Leu Asp Gln Ala
        35                  40                  45

Pro Glu Gly Arg Gly Trp Arg Arg Leu Ala Glu Leu Ala Gly Ser Arg
    50                  55                  60

Gly Arg Leu Arg Leu Ser Cys Leu Asp Leu Glu Gln Cys Ser Leu Lys
65                  70                  75                  80

Val Leu Glu Pro Glu Gly Ser Pro Ser Leu Cys Leu Leu Lys Leu Met
                85                  90                  95

Gly Glu Lys Gly Cys Thr Val Thr Glu Leu Ser Asp Phe Leu Gln Ala
            100                 105                 110

Met Glu His Thr Glu Val Leu Gln Leu Leu Ser Pro Pro Gly Ile Lys
        115                 120                 125

Ile Thr Val Asn Pro Glu Ser Lys Ala Val Leu Ala Gly Gln Phe Val
    130                 135                 140

Lys Leu Cys Cys Arg Ala Thr Gly His Pro Phe Val Gln Tyr Gln Trp
145                 150                 155                 160

Phe Lys Met Asn Lys Glu Ile Pro Asn Gly Asn Thr Ser Glu Leu Ile
                165                 170                 175

Phe Asn Ala Val His Val Lys Asp Ala Gly Phe Tyr Val Cys Arg Val
            180                 185                 190

Asn Asn Asn Phe Thr Phe Glu Phe Ser Gln Trp Ser Gln Leu Asp Val
        195                 200                 205

Cys Asp Ile Pro Glu Ser Phe Gln Arg Ser Val Asp Gly Val Ser Glu
    210                 215                 220
```

-continued

```
Ser Lys Leu Gln Ile Cys Val Glu Pro Thr Ser Gln Lys Leu Met Pro
225                 230                 235                 240
Gly Ser Thr Leu Val Leu Gln Cys Val Ala Val Gly Ser Pro Ile Pro
                245                 250                 255
His Tyr Gln Trp Phe Lys Asn Glu Leu Pro Leu Thr His Glu Thr Lys
            260                 265                 270
Lys Leu Tyr Met Val Pro Tyr Val Asp Leu Glu His Gln Gly Thr Tyr
        275                 280                 285
Trp Cys His Val Tyr Asn Asp Arg Asp Ser Gln Asp Ser Lys Lys Val
    290                 295                 300
Glu Ile Ile Ile Gly Arg Thr Asp Glu Ala Val Glu Cys Thr Glu Asp
305                 310                 315                 320
Glu Leu Asn Asn Leu Gly His Pro Asp Asn Lys Glu Gln Thr Thr Asp
                325                 330                 335
Gln Pro Leu Ala Lys Asp Lys Val Ala Leu Leu Ile Gly Asn Met Asn
                340                 345                 350
Tyr Arg Glu His Pro Lys Leu Lys Ala Pro Leu Val Asp Val Tyr Glu
        355                 360                 365
Leu Thr Asn Leu Leu Arg Gln Leu Asp Phe Lys Val Val Ser Leu Leu
    370                 375                 380
Asp Leu Thr Glu Tyr Glu Met Arg Asn Ala Val Asp Glu Phe Leu Leu
385                 390                 395                 400
Leu Leu Asp Lys Gly Val Tyr Gly Leu Leu Tyr Tyr Ala Gly His Gly
                405                 410                 415
Tyr Glu Asn Phe Gly Asn Ser Phe Met Val Pro Val Asp Ala Pro Asn
            420                 425                 430
Pro Tyr Arg Ser Glu Asn Cys Leu Cys Val Gln Asn Ile Leu Lys Leu
        435                 440                 445
Met Gln Glu Lys Glu Thr Gly Leu Asn Val Phe Leu Leu Asp Met Cys
    450                 455                 460
Arg Lys Arg Asn Asp Tyr Asp Asp Thr Ile Pro Ile Leu Asp Ala Leu
465                 470                 475                 480
Lys Val Thr Ala Asn Ile Val Phe Gly Tyr Ala Thr Cys Gln Gly Ala
                485                 490                 495
Glu Ala Phe Glu Ile Gln His Ser Gly Leu Ala Asn Gly Ile Phe Met
            500                 505                 510
Lys Phe Leu Lys Asp Arg Leu Leu Glu Asp Lys Lys Ile Thr Val Leu
        515                 520                 525
Leu Asp Glu Val Ala Glu Asp Met Gly Lys Cys His Leu Thr Lys Gly
    530                 535                 540
Lys Gln Ala Leu Glu Ile Arg Ser Ser Leu Ser Glu Lys Arg Ala Leu
545                 550                 555                 560
Thr Asp Pro Ile Gln Gly Thr Glu Tyr Ser Ala Glu Ser Leu Val Arg
                565                 570                 575
Asn Leu Gln Trp Ala Lys Ala His Glu Leu Pro Glu Ser Met Cys Leu
            580                 585                 590
Lys Phe Asp Cys Gly Val Gln Ile Gln Leu Gly Phe Ala Ala Glu Phe
        595                 600                 605
Ser Asn Val Met Ile Ile Tyr Thr Ser Ile Val Tyr Lys Pro Pro Glu
    610                 615                 620
Ile Ile Met Cys Asp Ala Tyr Val Thr Asp Phe Pro Leu Asp Leu Asp
625                 630                 635                 640
Ile Asp Pro Lys Asp Ala Asn Lys Gly Thr Pro Glu Glu Thr Gly Ser
```

```
                    645                 650                 655
Tyr Leu Val Ser Lys Asp Leu Pro Lys His Cys Leu Tyr Thr Arg Leu
                660                 665                 670

Ser Ser Leu Gln Lys Leu Lys Glu His Leu Val Phe Thr Val Cys Leu
            675                 680                 685

Ser Tyr Gln Tyr Ser Gly Leu Glu Asp Thr Val Glu Asp Lys Gln Glu
        690                 695                 700

Val Asn Val Gly Lys Pro Leu Ile Ala Lys Leu Asp Met His Arg Gly
705                 710                 715                 720

Leu Gly Arg Lys Thr Cys Phe Gln Thr Cys Leu Met Ser Asn Gly Pro
                725                 730                 735

Tyr Gln Ser Ser Ala Ala Thr Ser Gly Gly Ala Gly His Tyr His Ser
            740                 745                 750

Leu Gln Asp Pro Phe His Gly Val Tyr His Ser His Pro Gly Asn Pro
        755                 760                 765

Ser Asn Val Thr Pro Ala Asp Ser Cys His Cys Ser Arg Thr Pro Asp
770                 775                 780

Ala Phe Ile Ser Ser Phe Ala His His Ala Ser Cys His Phe Ser Arg
785                 790                 795                 800

Ser Asn Val Pro Val Glu Thr Thr Asp Glu Ile Pro Phe Ser Phe Ser
                805                 810                 815

Asp Arg Leu Arg Ile Ser Glu Lys
            820

<210> SEQ ID NO 3
<211> LENGTH: 5013
<212> TYPE: DNA
<213> ORGANISM: human

<400> SEQUENCE: 3
cgaggctccg tgccccgccc cccgggtgcc ccgccccttt gcgcggctgg cgcggccagc     60
aggccaggct cccctcggca aacctgtcta attggggcgg ggagcggagc ttcctcctct    120
gagggccgtg ccgcgctgcc agatttgttc ttccgcccct gcctccgcgg ctcggaggcg    180
agcggaaggt gccccggggc cgaggcccgt gacggggcgg gcgggagccc cggcagtccg    240
gggtcgccgg cgagggccat gtcgctgttg ggggacccgc tacaggccct gccgccctcg    300
gccgccccca cggggccgct gctcgcccct ccggccggcg cgaccctcaa ccgcctgcgg    360
gagccgctgc tgcggaggct cagcgagctc ctggatcagg cgcccgaggg ccggggctgg    420
aggagactgg cggagctggc ggggagtcgc gggcgcctcc gcctcagttg cctagacctg    480
gagcagtgtt ctcttaaggt actggagcct gaaggaagcc ccagcctgtg tctgctgaag    540
ttaatgggtg aaaaaggttg cacagtcaca gaattgagtg atttcctgca ggctatggaa    600
cacactgaag ttcttcagct tctcagcccc ccaggaataa agattactgt aaacccagag    660
tcaaaggcag tcttggctgg acagtttgtg aaactgtgtt gccgggcaac tggacatcct    720
tttgttcaat atcagtggtt caaaatgaat aaagagattc caaatggaaa tacatcagag    780 cttatttta atgcagtgca tgtaaaagat gcaggctttt atgtctgtcg agttaataac    840
aatttcacct ttgaattcag ccagtggtca cagctggatc tttgcgacat cccagagagc    900
ttccagagaa gtgttgatgg cgtctctgaa tccaagttgc aaatctgtgt tgaaccaact    960
tcccaaaagc tgatgccagg cagcacattg gttttacagt gtgttgctgt tggaagcccc   1020
attcctcact accagtggtt caaaaatgaa ttaccattaa cacatgagac caaaaagcta   1080
```

```
tacatggtgc cttatgtgga tttggaacac caaggaacct actggtgtca tgtatataat    1140
gatcgagaca gtcaagatag caagaaggta gaaatcatca tagatgaatt aaataatctt    1200
ggtcatcctg ataataaaga gcaaacaact gaccagcctt tggcgaagga caaggttgcc    1260
cttttgatag gaaatatgaa ttaccgggag caccccaagc tcaaagctcc tttggtggat    1320
gtgtacgaat tgactaactt actgagacag ctggacttca aagtggtttc actgttggat    1380
cttactgaat atgagatgcg taatgctgtg gatgagtttt tactccttt agacaaggga    1440 gtatatgggt tattatatta tgcaggacat ggttatgaaa attttgggaa cagcttcatg    1500
gtccccgttg atgctccaaa tccatatagg tctgaaaatt gtctgtgtgt acaaaatata    1560
ctgaaattga tgcaagaaaa agaaactgga cttaatgtgt cttattgga tatgtgtagg     1620 aaaagaaatg actacgatga taccattcca atcttggatg cactaaaagt caccgccaat    1680
attgtgtttg gatatgccac gtgtcaagga gcagaagctt ttgaaatcca gcattctgga    1740
ttggcaaatg gaatctttat gaaattttta aagacagat tattagaaga taagaaaatc     1800
actgtgttac tggatgaagt tgcagaagat atgggtaagt gtcaccttac caaaggcaaa    1860
caggctctag agattcgaag tagtttatct gagaagagag cacttactga tccaatacag    1920
ggaacagaat attctgctga atctcttgtg cggaatctac agtgggccaa ggctcatgaa    1980
cttccagaaa gtatgtgtct taagtttgac tgtggtgttc agattcaatt aggatttgca    2040
gctgagtttt ccaatgtcat gatcatctat acaagtatag tttacaaacc accggagata    2100
ataatgtgtg atgcctacgt tactgatttt ccacttgatc tagatattga tccaaaagat    2160
gcaaataaag gcacacctga agaaactggc agctacttgg tatcaaagga tcttcccaag    2220
cattgcctct ataccagact cagttcactg caaaaattaa aggaacatct agtcttcaca    2280
gtatgtttat catatcagta ctcaggattg gaagatactg tagaggacaa gcaggaagtg    2340
aatgttggga aacctctcat tgctaaatta gacatgcatc gaggtttggg aaggaagact    2400
tgctttcaaa cttgtcttat gtctaatggt ccttaccaga gttctgcagc cacctcagga    2460
ggagcagggc attatcactc attgcaagac ccattccatg gtgtttacca ttcacatcct    2520
ggtaatccaa gtaatgttac accagcagat agctgtcatt gcagccggac tccagatgca    2580
tttatttcaa gtttcgctca ccatgcttca tgtcatttta gtagaagtaa tgtgccagta    2640
gagacaactg atgaaatacc atttagtttc tctgacaggc tcagaatttc tgaaaaatga    2700
cctccttgtt tttgaaagtt agcataattt tagatgcctg tgaaatagta ctgcacttac    2760
ataaagtgag acattgtgaa aaggcaaatt tgtatatgta gagaaagaat agtagtaact    2820
gtttcatagc aaacttcagg actttgagat gttgaaatta cattatttaa ttacagactt    2880
cctcttccta agattttgtg aattggttga atagttctat acaaatgaag tatggaggtg    2940
tgtatgttta tatgtatata acaaaatatt ttcattgtga ccactctgaa gtaagagcaa    3000
tgggaatggc attattgtag aataagtcat tgtattttta acaccagaaa gaaccttgcc    3060
gatcaccagg cataacctaa ttttatccat ggaagaaaca cagaaaggca tctaagttag    3120
agctggcacc agaactgaga cctccagaaa tctattccag tattttttcc actacacaac    3180
tgccttcctg acaggttctg agataagtgt tatgtttgta gatagagtga atatatttta    3240
tatatatata aatatataca gatacatatc tgtgtattat ctcaaggaat gtacaaactt    3300 tagttttga ttataaggac ttcactgcaa gttttagtta agaggtttgt atataaatct      3360
gttatagaac aggctgaaat ttcttgttca taagattatg aaaccacatg agaagtgata    3420
aaatgtttgt taaagctaga tagaggttaa gaatcaagat ataatggata attttcatag    3480
```

```
ctgcctatca gaatttccca aatatttagc atcttccttg ataatatgta ttttcttctt   3540
gaatttcact ggcctaatga gataatactc ttatctttgg ctctacctaa aagttggtta   3600
aaaatgcaat tggcattaac aaggaaaaat actgaattag taattttaaa agtctcacaa   3660
agaaaatccc aggcctagat ggctgcattg ttgaattctg ccaaacatta aaattagcac   3720
taattttttg cacactgttt ctaaaagtag gagaggaaag aacacttccc aacttactct   3780
aggtcagtat taccctgata ctagactaga catcacaaga aaactataag ccaatattcc   3840
ttattaatac aaacacaaaa atcattaaca aaaatattag caaactgaat ccagcaacct   3900
ataaaaagga ttctatatca tgaccaagtg gaatttatcc caggaattca aggttggttc   3960
aacatctaaa aatcaaataa gctaatatac agtcagttct cattattcac agtaattatg   4020
ttctacagaa tattctccca taaacactga attaaatatg gaacaactgc ttttaggaga   4080
aagtgtattt gtgtatatgt gtgtatacat atgtttatct cacacacatt atgagcttga   4140
attcttaatt catcctagca aattctacct tattttacag aagtgaaagt gaggtatcag   4200
aagtgttaag tgacatgcct gaggcacccc cctaacaggt gtcagagctg aaattcaaac   4260
cccatccagc tggccccgga gccagagctt cttgtactac acagaattgc ccctgccatt   4320
tccaccctcc agtcatttct ctatgagact gaagcaggaa ggcagagcat catcttgttc   4380
agcctcagct gggaacatgt gtactgggtg actcaaattt ttcacccatt tacacatatc   4440
cacaaatgac tgcaaaagtg ccacggatat caatttgagg gttataaatt ttagcaagtt   4500
ggtaaattca caaatacata accttgaata atgaggatca actgtaccat atttaataaa   4560
gcacaaaacc cacacagatt gtcttattac agcatttgat aaaatccaaa actctttcat   4620
aaaaacactc aacaaactta ggaataaaag gaatcttcct agatatgata aatataacat   4680
ctatgaaaag cccacaccta acattatact tcatggtgat agactgaagg ctgaatgttt   4740 tcccctttaag attgggaaga aggacaagga tgttcactcg gcactacttc tattcagcat   4800
tgtacttgaa gttctagcca cagcagttag gttaggaatt caaggtttgt tcaacatcta   4860
aaaatcaaat aagctaataa agaaagagg tttatactgc aaaagaagtg aaactatatg   4920
tattcacagt tgatacatag ttgtatatag aaaatgctaa agaatccata aaaagtaata   4980
aatgagttca acaggttaaa aaaaaaaaaa aaa                                5013
```

<210> SEQ ID NO 4
<211> LENGTH: 813
<212> TYPE: PRT
<213> ORGANISM: human

<400> SEQUENCE: 4

Met Ser Leu Leu Gly Asp Pro Leu Gln Ala Leu Pro Pro Ser Ala Ala
1               5                   10                  15

Pro Thr Gly Pro Leu Leu Ala Pro Pro Ala Gly Ala Thr Leu Asn Arg
            20                  25                  30

Leu Arg Glu Pro Leu Leu Arg Arg Leu Ser Glu Leu Leu Asp Gln Ala
        35                  40                  45

Pro Glu Gly Arg Gly Trp Arg Arg Leu Ala Glu Leu Ala Gly Ser Arg
    50                  55                  60

Gly Arg Leu Arg Leu Ser Cys Leu Asp Leu Glu Gln Cys Ser Leu Lys
65                  70                  75                  80

Val Leu Glu Pro Glu Gly Ser Pro Ser Leu Cys Leu Leu Lys Leu Met
                85                  90                  95

-continued

```
Gly Glu Lys Gly Cys Thr Val Thr Glu Leu Ser Asp Phe Leu Gln Ala
            100                 105                 110

Met Glu His Thr Glu Val Leu Gln Leu Leu Ser Pro Pro Gly Ile Lys
            115                 120                 125

Ile Thr Val Asn Pro Glu Ser Lys Ala Val Leu Ala Gly Gln Phe Val
130                 135                 140

Lys Leu Cys Cys Arg Ala Thr Gly His Pro Phe Val Gln Tyr Gln Trp
145                 150                 155                 160

Phe Lys Met Asn Lys Glu Ile Pro Asn Gly Asn Thr Ser Glu Leu Ile
                165                 170                 175

Phe Asn Ala Val His Val Lys Asp Ala Gly Phe Tyr Val Cys Arg Val
            180                 185                 190

Asn Asn Asn Phe Thr Phe Glu Phe Ser Gln Trp Ser Gln Leu Asp Val
            195                 200                 205

Cys Asp Ile Pro Glu Ser Phe Gln Arg Ser Val Asp Gly Val Ser Glu
210                 215                 220

Ser Lys Leu Gln Ile Cys Val Glu Pro Thr Ser Gln Lys Leu Met Pro
225                 230                 235                 240

Gly Ser Thr Leu Val Leu Gln Cys Val Ala Val Gly Ser Pro Ile Pro
                245                 250                 255

His Tyr Gln Trp Phe Lys Asn Glu Leu Pro Leu Thr His Glu Thr Lys
            260                 265                 270

Lys Leu Tyr Met Val Pro Tyr Val Asp Leu Glu His Gln Gly Thr Tyr
                275                 280                 285

Trp Cys His Val Tyr Asn Asp Arg Asp Ser Gln Asp Ser Lys Lys Val
            290                 295                 300

Glu Ile Ile Ile Asp Glu Leu Asn Asn Leu Gly His Pro Asp Asn Lys
305                 310                 315                 320

Glu Gln Thr Thr Asp Gln Pro Leu Ala Lys Asp Lys Val Ala Leu Leu
                325                 330                 335

Ile Gly Asn Met Asn Tyr Arg Glu His Pro Lys Leu Lys Ala Pro Leu
            340                 345                 350

Val Asp Val Tyr Glu Leu Thr Asn Leu Leu Arg Gln Leu Asp Phe Lys
            355                 360                 365

Val Val Ser Leu Leu Asp Leu Thr Glu Tyr Glu Met Arg Asn Ala Val
            370                 375                 380

Asp Glu Phe Leu Leu Leu Leu Asp Lys Gly Val Tyr Gly Leu Leu Tyr
385                 390                 395                 400

Tyr Ala Gly His Gly Tyr Glu Asn Phe Gly Asn Ser Phe Met Val Pro
                405                 410                 415

Val Asp Ala Pro Asn Pro Tyr Arg Ser Glu Asn Cys Leu Cys Val Gln
            420                 425                 430

Asn Ile Leu Lys Leu Met Gln Glu Lys Glu Thr Gly Leu Asn Val Phe
            435                 440                 445

Leu Leu Asp Met Cys Arg Lys Arg Asn Asp Tyr Asp Asp Thr Ile Pro
450                 455                 460

Ile Leu Asp Ala Leu Lys Val Thr Ala Asn Ile Val Phe Gly Tyr Ala
465                 470                 475                 480

Thr Cys Gln Gly Ala Glu Ala Phe Glu Ile Gln His Ser Gly Leu Ala
                485                 490                 495

Asn Gly Ile Phe Met Lys Phe Leu Lys Asp Arg Leu Leu Glu Asp Lys
            500                 505                 510

Lys Ile Thr Val Leu Leu Asp Glu Val Ala Glu Asp Met Gly Lys Cys
```

```
            515                 520                 525

His Leu Thr Lys Gly Lys Gln Ala Leu Glu Ile Arg Ser Ser Leu Ser
    530                 535                 540

Glu Lys Arg Ala Leu Thr Asp Pro Ile Gln Gly Thr Glu Tyr Ser Ala
545                 550                 555                 560

Glu Ser Leu Val Arg Asn Leu Gln Trp Ala Lys Ala His Glu Leu Pro
                565                 570                 575

Glu Ser Met Cys Leu Lys Phe Asp Cys Gly Val Gln Ile Gln Leu Gly
            580                 585                 590

Phe Ala Ala Glu Phe Ser Asn Val Met Ile Ile Tyr Thr Ser Ile Val
        595                 600                 605

Tyr Lys Pro Pro Glu Ile Ile Met Cys Asp Ala Tyr Val Thr Asp Phe
    610                 615                 620

Pro Leu Asp Leu Asp Ile Asp Pro Lys Asp Ala Asn Lys Gly Thr Pro
625                 630                 635                 640

Glu Glu Thr Gly Ser Tyr Leu Val Ser Lys Asp Leu Pro Lys His Cys
                645                 650                 655

Leu Tyr Thr Arg Leu Ser Ser Leu Gln Lys Leu Lys Glu His Leu Val
            660                 665                 670

Phe Thr Val Cys Leu Ser Tyr Gln Tyr Ser Gly Leu Glu Asp Thr Val
        675                 680                 685

Glu Asp Lys Gln Glu Val Asn Val Gly Lys Pro Leu Ile Ala Lys Leu
    690                 695                 700

Asp Met His Arg Gly Leu Gly Arg Lys Thr Cys Phe Gln Thr Cys Leu
705                 710                 715                 720

Met Ser Asn Gly Pro Tyr Gln Ser Ser Ala Ala Thr Ser Gly Gly Ala
                725                 730                 735

Gly His Tyr His Ser Leu Gln Asp Pro Phe His Gly Val Tyr His Ser
            740                 745                 750

His Pro Gly Asn Pro Ser Asn Val Thr Pro Ala Asp Ser Cys His Cys
        755                 760                 765

Ser Arg Thr Pro Asp Ala Phe Ile Ser Ser Phe Ala His His Ala Ser
    770                 775                 780

Cys His Phe Ser Arg Ser Asn Val Pro Val Glu Thr Thr Asp Glu Ile
785                 790                 795                 800

Pro Phe Ser Phe Ser Asp Arg Leu Arg Ile Ser Glu Lys
                805                 810

<210> SEQ ID NO 5
<211> LENGTH: 4
<212> TYPE: PRT
<213> ORGANISM: Artificial Sequence
<220> FEATURE:
<223> OTHER INFORMATION: Peptide

<400> SEQUENCE: 5

Leu Arg Ser Arg
1

<210> SEQ ID NO 6
<211> LENGTH: 4
<212> TYPE: PRT
<213> ORGANISM: Artificial Sequence
<220> FEATURE:
<223> OTHER INFORMATION: Peptide

<400> SEQUENCE: 6
```

Val Arg Pro Arg
1

<210> SEQ ID NO 7
<211> LENGTH: 4
<212> TYPE: PRT
<213> ORGANISM: Artificial Sequence
<220> FEATURE:
<223> OTHER INFORMATION: Peptide

<400> SEQUENCE: 7

Leu Val Ser Arg
1

<210> SEQ ID NO 8
<211> LENGTH: 4
<212> TYPE: PRT
<213> ORGANISM: Artificial Sequence
<220> FEATURE:
<223> OTHER INFORMATION: Peptide

<400> SEQUENCE: 8

Phe Met Ser Arg
1

<210> SEQ ID NO 9
<211> LENGTH: 4
<212> TYPE: PRT
<213> ORGANISM: Artificial Sequence
<220> FEATURE:
<223> OTHER INFORMATION: Peptide

<400> SEQUENCE: 9

Cys Leu Ser Arg
1

<210> SEQ ID NO 10
<211> LENGTH: 4
<212> TYPE: PRT
<213> ORGANISM: Artificial Sequence
<220> FEATURE:
<223> OTHER INFORMATION: Peptide

<400> SEQUENCE: 10

Gly Ala Ser Arg
1

<210> SEQ ID NO 11
<211> LENGTH: 5
<212> TYPE: PRT
<213> ORGANISM: Artificial Sequence
<220> FEATURE:
<223> OTHER INFORMATION: Peptide

<400> SEQUENCE: 11

Ala Leu Val Ser Arg
1               5

<210> SEQ ID NO 12
<211> LENGTH: 4
<212> TYPE: PRT
<213> ORGANISM: Artificial Sequence
<220> FEATURE:
<223> OTHER INFORMATION: Peptide

<400> SEQUENCE: 12

Asp Glu Val Asp
1

```
<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
ucacuguguu acuggauga                                                19
```

MEANS AND METHODS FOR DETECTING ACTIVATED MALT1

TECHNICAL FIELD OF THE INVENTION

The present invention provides means and methods for selectively detecting activated MALT1 in a sample. Moreover, the present invention provides a method for diagnosing diseases, which are characterized by an increased MALT1 activity. Finally, the present invention provides methods for identifying patients which are amenable to treatment with a therapeutic agent capable of inhibiting MALT1 activity.

SEQUENCE LISTING

The instant application contains a sequence listing (.txt file named SequenceListing, generated on May 17, 2018 and is 28.924 bytes in size) which has been submitted in ASCII format via EFS-Web and is incorporated by reference herein.

BACKGROUND OF THE INVENTION

MALT1 paracaspase is a cysteine protease and contains a caspase-like domain that is structurally highly homologous to classical caspases [10, 11]. However, in contrast to caspases, MALT1 displays a high preference for arginine in the P1 position [12], which is common for metacaspases found in protozoa, fungi and plants [13]. Activation of cellular MALT1 depends on a conformational change within the paracaspase domain and a monoubiquitination in the C-terminal Ig3 domain of MALT1 [14]. Activation of MALT1 is required for an optimal induction of adaptive immunity [15-17]. In resting lymphocytes MALT1 is in an inactive state and its activity is rapidly induced upon T cell receptor (TCR)/CD28 co-stimulation. Unbalanced MALT1 activity is considered to promote autoimmune diseases, e.g. experimental autoimmune encephalitis (EAE) which is a murine model for Multiple Sclerosis [18, 19]. Further chronic MALT1 activity delivers a critical survival signal in distinct malignant lymphomas, such as the activated B cell type of diffuse large B cell lymphoma (ABC DLBCL), mucosa associated lymphoid tissue (MALT) lymphoma [20-22] or mantle cell lymphoma (MCL)[4]. Hence, MALT1 is a promising therapeutic target for autoimmune diseases and cancer and the first small molecule MALT1 inhibitors have recently been identified [23, 24].

To date, determination of cellular MALT1 activity relies either on the measurement of in vitro MALT1 activity after immunoprecipitation (IP) or the detection of cleaved substrates, e.g. RelB, A20, CYLD or BCL10 [15, 17, 25]. Here, we introduce a chemical approach for selective detection of active MALT1.

SUMMARY OF THE INVENTION

In one aspect, the present invention relates to a method for the detection of activated MALT1 in a test sample comprising the steps of:
(a) contacting a test sample with a diagnostic inhibitor of MALT1 activity under conditions allowing the formation of a MALT1 complex of said diagnostic inhibitor and activated MALT1; and
(b) qualitative and/or quantitative detection of the MALT1 complex by a first detection agent, which binds to a first binding site on the MALT1 complex of (a),
wherein said diagnostic inhibitor comprises the following covalently linked subunits:

(i) a first subunit comprising at least one detectable label,
(ii) a second subunit comprising a peptide or polypeptide capable of binding to the catalytic center of activated MALT1, and
(iii) a third subunit comprising at least one moiety for linking the diagnostic inhibitor to activated MALT1.

In one embodiment of the present invention, the qualitative and/or quantitative detection of the MALT1 complex comprises detection by a second detection agent that binds to a second binding site on the MALT1 complex.

In another embodiment of the present invention, the second detection agent comprises a MALT1 antibody or an antigen binding fragment of said antibody and a detectable label.

In another embodiment of the present invention, the detectable label of the second detection agent is coupled to the MALT1 antibody or to an antibody, which is capable of binding to said MALT1 antibody.

In another embodiment of the present invention, the first detection agent is linked to a solid support.

In another embodiment of the present invention, the first subunit of the diagnostic MALT1 inhibitor is or comprises a detectable label selected from the group consisting of biotin, glutathione, peptide comprising at least 6 histidines, glycosylated peptide, metalloprotein, metal, $Co^{2+}$, $Ni^{2+}$, $Cu^{2+}$, and $Zn^{2+}$, chromophore, fluorophore, radioisotope, Iodine125 ($^{125}$I) and affinity tag.

In another embodiment of the present invention, the first detection agent is selected from the group consisting of avidin, streptavidin, StrepTactin, HA, FLAG, GST or a functional fragment of GST, a peptide comprising at least 6 histidines, lectin and an antibody capable of binding to the detectable label.

In another embodiment of the present invention, the second subunit of the diagnostic inhibitor is or comprises a tetrapeptide, preferably selected from LRSR (SEQ ID No. 5), VRPR (SEQ ID No. 6), LVSR (SEQ ID No. 7), FMSR (SEQ ID No. 8, CLSR (SEQ ID No. 9) and GASR (SEQ ID No. 10).

In another embodiment of the present invention, said second subunit is a pentapeptide, preferably the pentapeptide ALVSR (SEQ ID No. 11).

In another embodiment of the present invention, the third subunit of the diagnostic inhibitor is or comprises an acyloxymethyl ketone (AOMK), fluoromethlyketone (FMK), diazomethylketone, O-acylhydroxylamine, vinyl sulfone, epoxysuccinyl derivate or chloromethlyketone (CMK).

In another aspect the present invention relates to a diagnostic inhibitor comprising the following covalently linked subunits:
(i) a first subunit comprising at least one detectable label,
(ii) a second subunit comprising a peptide or polypeptide capable of binding to the catalytic center of activated MALT1, and
(iii) a third subunit comprising at least one moiety for linking the diagnostic inhibitor to activated MALT1.

In another aspect the present invention relates to a method of detecting or diagnosing a disease or a predisposition for developing a disease, said disease being characterized by an increased MALT1 activity, said method comprising the steps of:
(a) qualitative and/or quantitative detection of activated MALT1 of a test sample and of a reference sample by performing the method of detection of the present invention;
(b) comparing the amount of activated MALT1 in the test sample and the reference sample; and (c) concluding from the observation of an increased amount of activated MALT1 in the test sample in comparison to the reference sample that the subject from which the test sample originates is affected from the disease or has a predisposition for the disease.

In one embodiment of the present invention, the disease is a tumor or cancer, an autoimmune disease or an inflammatory disease, such as multiple sclerosis, rheumatoid arthritis or a lymphoma, such as MALT lymphoma or a diffuse large B-cell lymphoma of the subtype ABC-DLBCL or a mantle cell lymphoma.

In another aspect the present invention relates to a method for monitoring a subject's response to a medication for treating a disease characterized by an increased MALT1 activity, comprising the steps of:
(a) qualitative and/or quantitative detection of activated MALT1 of a test sample and of a reference sample by performing the method of detection of the present invention, wherein the test sample is a sample obtained from the subject after treatment of the subject with a therapeutic agent and the reference sample is a sample obtained prior to the test sample, preferably before treatment of the subject with the therapeutic agent;
(b) comparing the amount of activated MALT1 in the test sample and the reference sample; and
(c) concluding from a reduced detectable amount of activated MALT1 in the test sample that the subject has responded to the therapeutic agent.

A method for monitoring a subject's response to a medication for treating a disease characterized by an increased MALT1 activity, comprising the steps of:
(a) qualitative and/or quantitative detection of activated MALT1 of a test sample and of a reference sample both originating from the same subject by performing the method of detection of the present application, wherein the test sample is a sample obtained from the subject after treatment or after a treatment step of the subject with a therapeutic agent and the reference sample is obtained before the treatment or the treatment step of the subject with the therapeutic agent;
(b) comparing the amount of activated MALT1 in the test sample and the reference sample; and
(c) concluding from a reduced detectable amount of activated MALT1 in the test sample in comparison with the reference sample whether the therapeutic agent effects a MALT1 response.

In another aspect the present invention relates to the use of the diagnostic inhibitor of the present invention for the preparation of a composition for diagnosing a disease or a predisposition to a disease, said disease being characterized by a requirement for MALT1 activity.

In another aspect the present invention relates to a kit for performing the methods of the present invention, wherein said kit comprises:
(i) the diagnostic inhibitor of the present invention and/or
(ii) a therapeutic agent capable of inhibiting MALT1 activity; and/or
(iii) instructions for use.

Finally, in another aspect the present invention relates to a MALT1 complex comprising a MALT 1 polypeptide and the diagnostic inhibitor of the present invention, wherein the MALT1 polypeptide, is encoded by a nucleic acid selected from the group consisting of:
(a) a nucleic acid which comprises a nucleic acid sequence as set forth in SEQ ID NO: 1 of the sequence listing or a part thereof; and
(b) a nucleic acid which has at least 50% sequence identity with the nucleic acid of (a) (SEQ ID NO: 1).

B) MALT1 wt and catalytic inactive mutant were overexpressed in Jurkat T cells and activity was measured in an in vitro cleavage assay. Catalytic activity is visualized by increasing fluorescence upon substrate cleavage. Results and SD from three independent experiments are shown.

C) MALT1 wt and mutant as well as A20 were overexpressed. MALT1 cleavage of A20, a natural substrate of MALT1, was analyzed by western blot. Both assays demonstrate that only wt MALT1 is capable of cleaving its substrates and that activity of overexpressed wt MALT1 is independent of stimulation. These data further demonstrate that high concentrations of MALT1 are sufficient to promote activation independent of stimulation.

Figure 3:
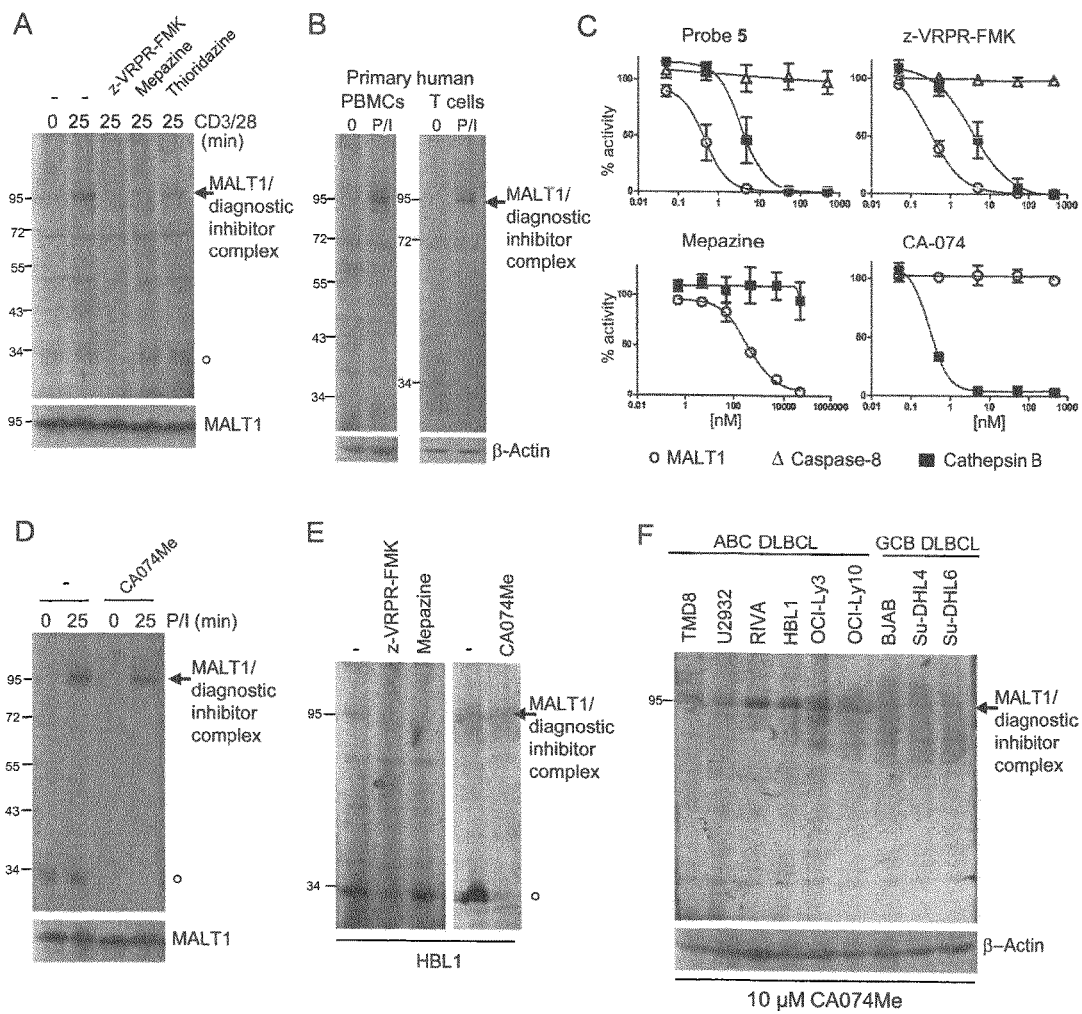

FIG. 3: A) Extracts of Jurkat T cells (CD3/28 stimulated or not) were stained with the diagnostic MALT1-inhibitor probe 5 (3 μM) and MALT1-inhibitor complex was visualized after SDS PAGE. MALT1 inhibition prevents binding of diagnostic MALT1-inhibitor: z-VRPR-FMK (SEQ ID NO: 6), mepazine or thioridazine (10 μM each) were incubated 1 h before stimulation; open circle indicates cathepsin B labeling.

B) Extracts of primary human PBMCs and T cells ($1\times10^7$ cells) were labeled with probe 5.

C) Impact of indicated compounds on MALT1, Caspase8 and cathepsin B was tested in in vitro cleavage assays using fluorescent substrates. Results and SD from three independent experiments are shown.

D) Jurkat T cells were pretreated with 10 μM CA-074Me, stimulated with P/I and extract was labeled with probe 5.

E) Active MALT1 staining with probe 6 in ABC DLBCL cell line HBL1. HBL1 cells after incubation of inhibitors (10 μM each) before detection of active MALT1.

F) Probe 6 can distinguish between ABC and GCB in extracts. Cells were pretreated with CA-074Me and labeling with probe 6 revealed constitutive MALT1 activity in ABC.

Figure 4:
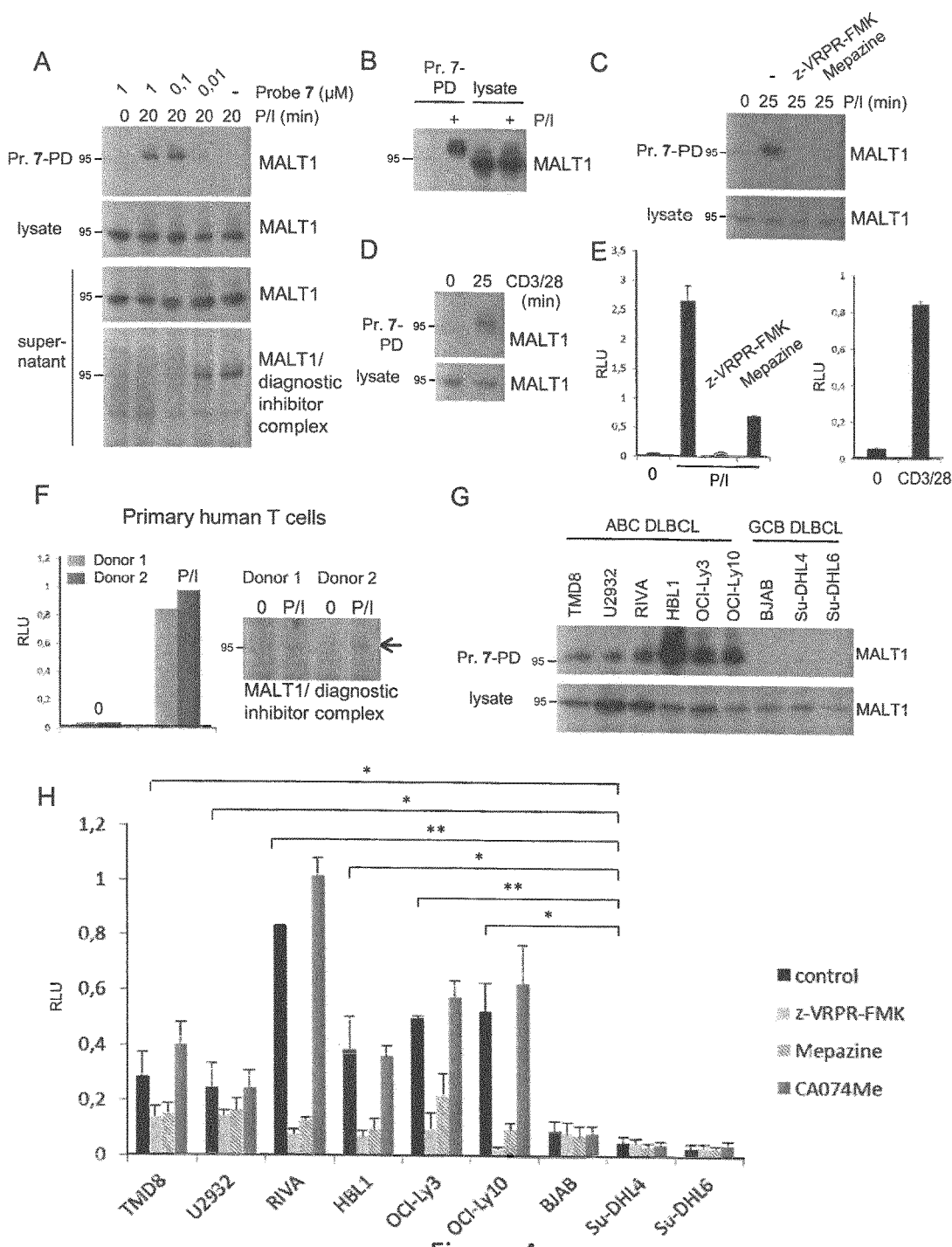

FIG. 4: Biotin-labeled diagnostic inhibitor (probe 7) for active MALT1 detection after pulldown (PD) and in ELISA-based reactions.

A) Jurkat T cells (stimulated or not) were lysed, incubated with different concentrations of probe 7, subjected to PD with streptavidin beads and analysed by SDS-PAGE and western blot. Supernatant was additionally analysed by probe 6 labeling and fluorescence scanning.

B) Probe 7-PD in Jurkat T cells was performed as in A), detecting the modified, active MALT1.

C) Jurkat T cells were pretreated with 10 μM inhibitors and pulldown was performed as in A) with 0.1 μM probe 7.

D) Probe 7-PD was performed as in C) after CD3/28 stimulation.

E) Jurkat T cells were treated with 10 μM inhibitors and stimulated as indicated. After lysis and probe 7 incubation (0.1 μM) transferred to streptavidin-coated plates and analysed by MALT1 antibody detection. Results and SD from three independent experiments are shown.

F) Primary human T cells ($2.5 \times 10^6$) were stimulated or not, incubated with either 3 μM probe 6 and analysed by fluorescence scanning or incubated with 0.1 μM probe 7 and analysed by ELISA-based assay.

G) Probe 7-PD of untreated DLBCL cells was performed as in B).

H) ELISA-based analysis of inhibitor-treated (10 μM) DLBCL cells was performed as in E). As an example, significance of differences are shown for all ABC DLBCL versus SUDHL4 cells as determined by a two-tailed t-test (<0.05 *; <0.005 **).

Figure 5:
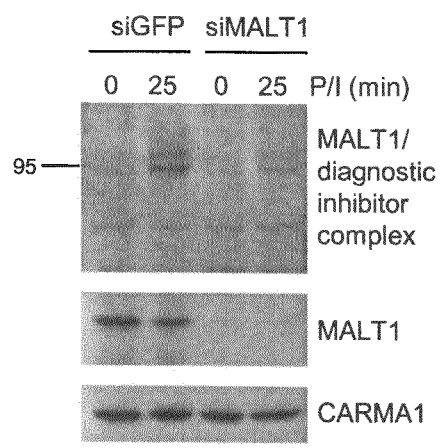

FIG. 5: Jurkat T cells were transfected with siRNA against MALT1 and siGFP as control for 72 hours. After stimulation and cell lysis, labeling with probe 6 was performed in whole cell extracts and analyzed after SDS PAGE by fluorescence scanning. Knock-down was checked by western blot FIG. 6: Jurkat T cells were stimulated or not, lysed and whole cell extract was incubated with indicated concentrations of FITC conjugated probe 5 or BODIPY conjugated probe 6 and analyzed via fluorescent scanning. Probe 6 results in slightly higher active MALT1 labeling and cathepsin labeling (open circle) seems to be reduced.

Figure 7:
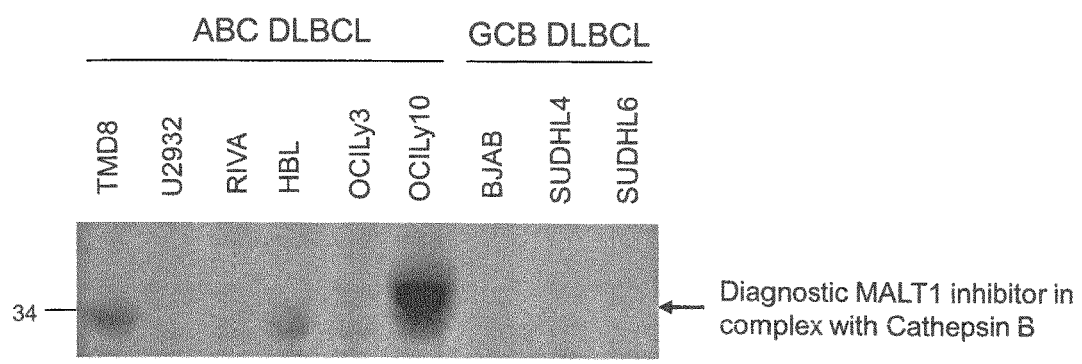

FIG. 7: Whole cell extracts of DLBCL cell lines were labeled with probe 6. Strong diagnostic inhibitor signals between 30-40 kDa most likely corresponding to cross-reactions with cysteine proteases of the cathepsin family are observed in some ABC DLBCL cell lines.

Figure 8:
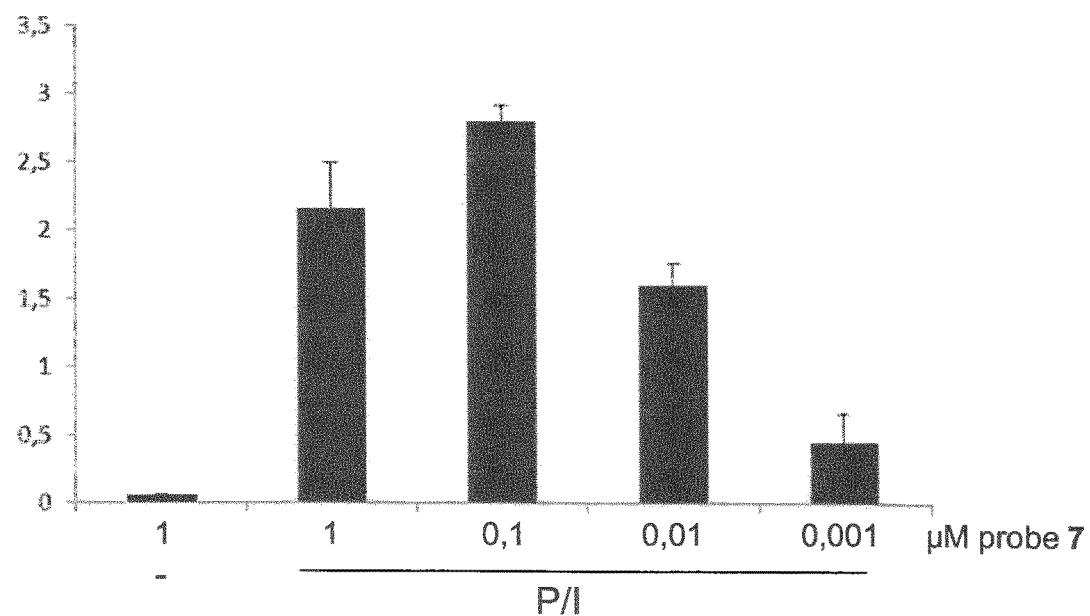

FIG. 8: $2 \times 10^6$ Jurkat T cells were stimulated or not, lysed, incubated with different concentrations of probe 7 and put on streptavidin-coated plates. Detection was performed via MALT1 antibody detection. Results from two independent experiments are shown.

Figure 9:
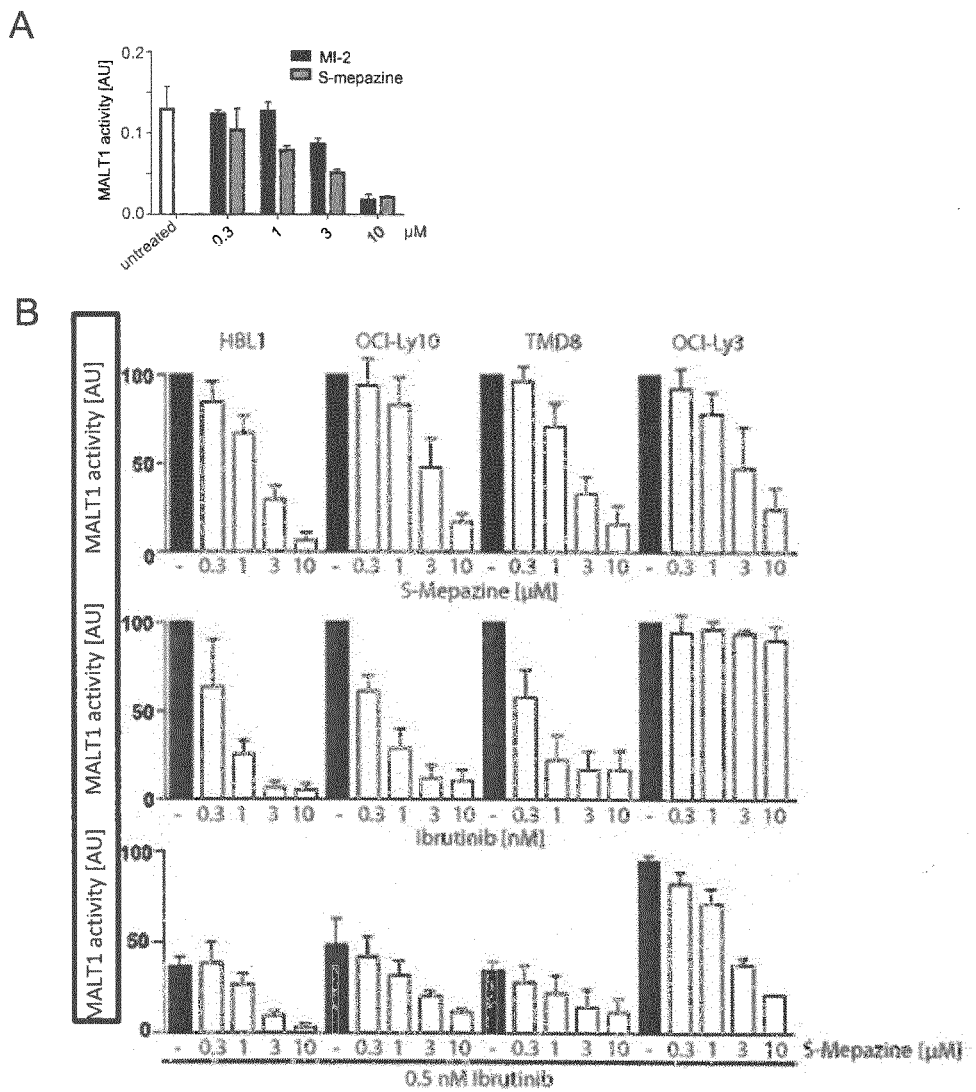

FIG. 9: A) Cellular inhibitor profiling in OCI-Ly3 cells. Cells were treated with depicted concentrations of MI-2 and S-mepazine, lysed, incubated with probe 7 and put on streptavidin-coated plates. Detection was performed by MALT1 antibody. B) MALT1 activity in ABC cell lines was analyzed as above after single or combinatorial treatment with ibrutinib and S-Mepazine with different concentrations as indicated. MALT1 activity is depicted as arbitrary units [AU].

Figure 10:
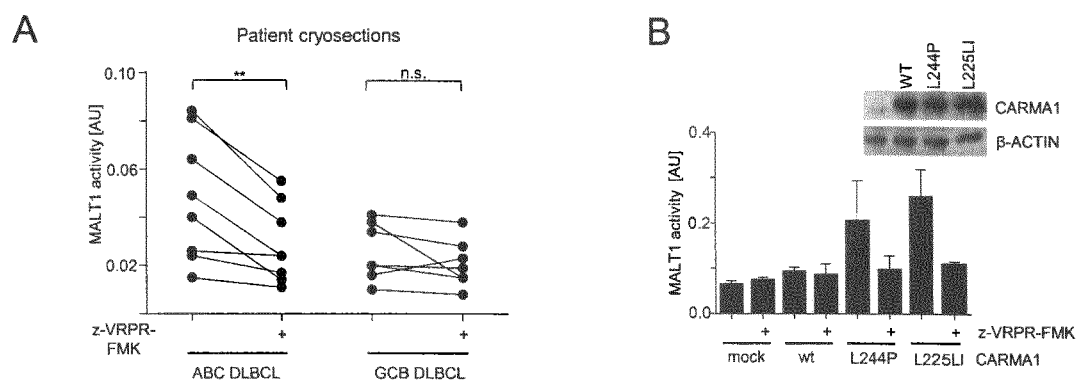

FIG. 10: A) Active MALT1 detection in cryo-preserved patient tumor samples. Frozen tumor tissue was lysed with a douncer and syringe, incubated with z-VRPR-FMK (0.25 μM) (SEQ ID No. 6) or left untreated before MALT1 activity read-out as above. Relative MALT1 activity from each untreated and z-VRPR-FMK (SEQ ID No. 6) treated samples was measured and directly compared (ABC DLBCL n=8; GCB DLBCL n=7). Significance for MALT1 activity in untreated to z-VRPR-FMK (SEQ ID No. 6) treated samples was calculated by a two-tailed t-test (**<0.005). B) Oncogenic CARMA1 is sufficient to trigger MALT1 activation. BJAB transduced with CARMA1 WT or L244P (ABC derived) or L225PI (GCB derived) were lysed and treated with z-VRPR-FMK (SEQ ID No. 6) and analyzed as above. Results and SD from three independent experiments are shown. MALT1 activity is depicted as arbitrary units [AU].

Figure 11:
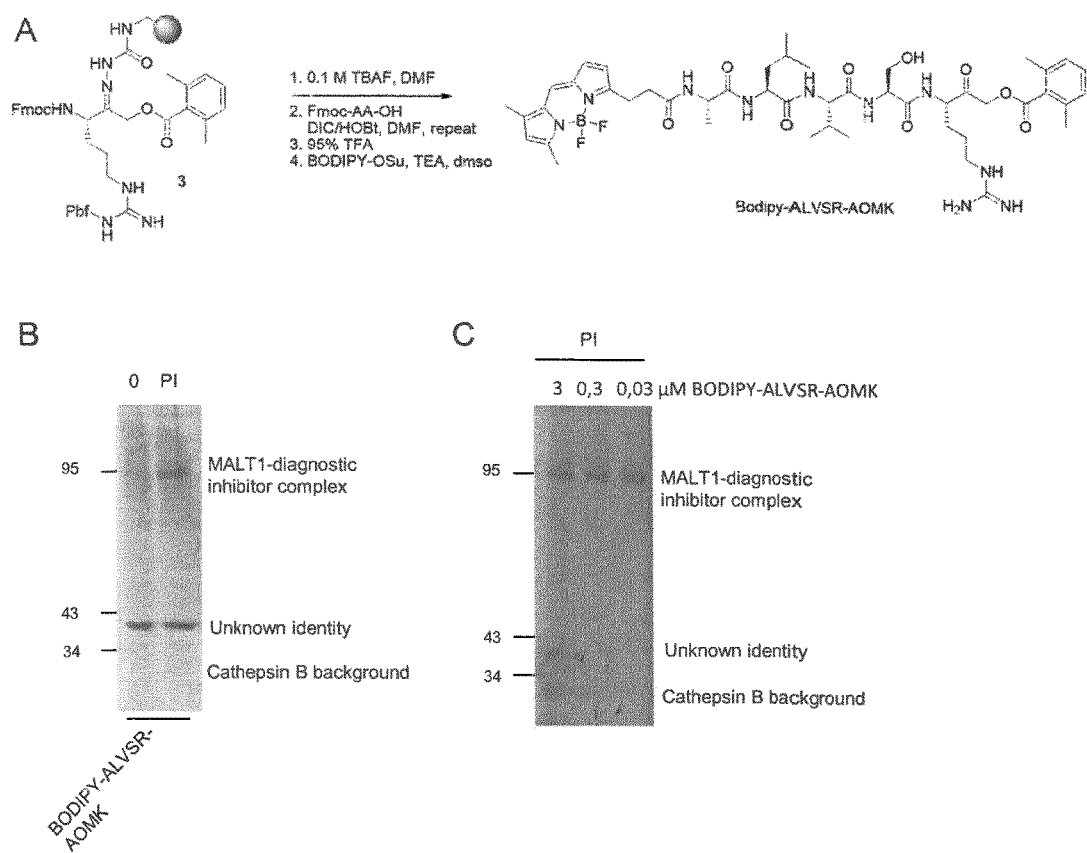

FIG. 11: A) Solid phase synthesis of the pentapeptide probe BODIPY-ALVSR-AOMK (SEQ ID No. 11) on resin starting from bound AOMK building block. B) Extracts from unstimulated or stimulated Jurkat T cells were stained with pentapeptide probe. Beside the induced active MALT1 signal, we observed an unknown background signal at around 40 kDa. C) We further titrated the pentapeptide probe in extracts of stimulated Jurkat T cells. Whereas MALT1 signal stays quite stable, background signals are attenuated with lower probe concentrations.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments, which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland (1995).

The practice of the present invention will employ, unless otherwise indicated, conventional methods of chemistry, biochemistry, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989; M. B. Smith and J. March, "March's advanced organic chemistry: reactions, mechanisms, and structure", 5th edition, John Wiley & Sons, Inc., 2001; "Organikum", 18th edition, Deutscher Verlag der Wissenschaften, 1990).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In a first aspect, the present invention relates to a diagnostic inhibitor of MALT1, which comprises the following covalently linked subunits:

(i) a first subunit comprising at least one detectable label, (ii) a second subunit comprising a peptide, polypeptide or peptidomimetic capable of binding to the catalytic center of activated MALT1, and (iii) a third subunit comprising at least one moiety for linking the diagnostic inhibitor to activated MALT1.

The expression "diagnostic inhibitor of MALT1" refers to a detectably labeled compound that is capable of forming a complex with MALT1, preferably by selectively binding to activated MALT1, and that is capable of inhibiting the proteolytic activity of MALT1.

The term "MALT1" refers to "Mucosa-associated lymphoid tissue lymphoma translocation protein 1". Preferably MALT1 is mammalian MALT1, for example of human origin or of chimpanzee, Rhesus monkey, mouse, rat, dog, cow, chicken. The term "MALT1", however, also refers to MALT1 of zebrafish and C. elegans. "MALT1" is used interchangeably with the term "MALT1 polypeptide". The term "MALT1" refers to isotype A and/or isotype B of MALT1. According to an alternative nomenclature "isotype A" is designated "isotype 1" and "isotype B" is designated "isotype 2". A nucleic acid sequence encoding isoform A of human MALT1 is described for example by the sequence deposited as NM_006785.3 (SEQ ID NO: 1). A nucleic acid sequence encoding isoform B of human MALT1 is described for example by the sequence deposited as NM_173844.2 (SEQ ID NO: 3). An amino acid sequence of isoform A of human MALT1 is described for example by the sequence deposited as A8K5S1 or is shown in NM_006785.3 (SEQ ID NO: 2). An amino acid sequence of isoform B of human MALT1 is described for example by the sequence deposited as A8K5S1 or is shown in NM_173844.2 (SEQ ID NO: 4).

As used herein, the term "MALT1" is or comprises a MALT1 polypeptide, which is encoded by a nucleic acid selected from the group consisting of:

(a) a nucleic acid which comprises a nucleic acid sequence as set forth in SEQ ID NO: 1 or 3 of the sequence listing or a part thereof;

(b) a nucleic acid which has at least 50%, 60%, 70%, 80%, 90%, 91%, 92%, 93%, 94%, 95%, 96%, 97%, 98% or 99% sequence identity with the nucleic acid of (a). Preferably, the nucleic acid encodes a functional variant of the MALT1 polypeptide encoded by the nucleic acid of (a).

In one embodiment, the nucleic acid encodes a polypeptide comprising the amino acid sequence as set forth in SEQ ID NO: 2 or 4 or a part thereof. In another embodiment, the nucleic acid encodes a polypeptide comprising an amino acid sequence which has at least 50%, 60%, 70%, 80%, 90%, 91%, 92%, 93%, 94%, 95%, 96%, 97%, 98% or 99% sequence identity with the amino acid sequence set forth in SEQ ID NO: 2 or 4. Preferably, the polypeptide is a functional variant of the MALT1 polypeptide as set forth in SEQ ID NO: 2 or 4.

The degree of nucleic acid sequence identity preferably refers to a region of at least about 300, at least about 400, at least about 450, at least about 500, at least about 550, at least about 600, at least about 650, at least about 700, at least about 750, or at least about 780 nucleotides. In preferred embodiments, the degree of sequence identity refers to the entire length of the reference nucleic acid sequence, such as the nucleic acid sequences given in the sequence listing.

The degree of amino acid sequence identity preferably refers to a region of at least about 100, at least about 120, at least about 140, at least about 160, at least about 180, at least about 200, at least about 220, at least about 240, at least about 250 or 260 amino acids. In preferred embodiments, the degree of identity refers to the entire length of the reference amino acid sequence such as the amino acid sequences provided by the sequence listing.

A "part" or a "fragment" of a nucleic acid coding for a MALT1 polypeptide relates according to the invention to the part of the nucleic acid, which codes at least for the MALT1 polypeptide or for a part or a fragment of said MALT1 polypeptide. A part or fragment of a nucleic acid coding for the MALT1 polypeptide is preferably that part of the nucleic acid corresponding to the open reading frame. A part or a fragment of the MALT1 polypeptide is preferably a functional part of the MALT1 polypeptide.

A part or fragment of the MALT1 polypeptide of the invention preferably comprises a sequence of at least 6, in particular at least 8, at least 10, at least 12, at least 15, at least 20, at least 30 or at least 50, at least 100 consecutive amino acids of the MALT1 polypeptide. A part or fragment of the MALT1 polypeptide of the invention preferably comprises a sequence of up to 8, in particular up to 10, up to 12, up to 15, up to 20, up to 30, up to 50, up to 100, or up to 150 consecutive amino acids of the MALT1 polypeptide.

According to the invention, the expression "functional part" or "functional fragment" or a "functional variant" of the MALT1 polypeptide refers to a MALT1 polypeptide or a part, fragment or variant thereof which is biologically active or which has a functional property of the polypeptide from which it has been derived. Such functional properties comprise for example the interaction with antibodies, the interaction with other polypeptides or proteins, and an enzymatic activity. Preferably the enzymatic activity comprises the proteolytic activity and substrate specificity of MALT1 according to SEQ ID NO: 2 or 4. Preferably the MALT1 polypeptide of the present invention is functionally active or biologically active if, in the cleavage assay described herein below, a conversion of at least 10%, 15%, 20%, 25% or 30% of substrate into cleavage product can be observed.

All of the above described sequences are within the scope of the present invention.

"Sequence identity" between two polypeptide or nucleic acid sequences indicates the percentage of amino acids or nucleotides that are identical between the sequences.

The "percentage identity" is obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

In one embodiment of the present invention, the term "MALT1" refers to isoform 1 of MALT1, a MALT1 polypeptide comprising 824 amino acid residues (Uniprot: Q9UDY8-1). In another embodiment, the term "MALT1" refers to isoform B of MALT1, a MALT1 polypeptide comprising 813 amino acid residues (Uniprot: Q9UDY8-2). Isoform B is a deletion variant of isoform A lacking amino acid residues 309 to 319 of isoform A resulting from an alternative splicing event.

The term "MALT1" also refers to fusion proteins comprising MALT1 or a part thereof comprising the paracaspase domain of MALT1. In addition, the fusion protein may comprise the Ig1, Ig2 and/or Ig3 domain of MALT1. API2-MALT1 is an example of a fusion protein comprising the paracaspase domain and the Ig2 and Ig3 domain of MALT1 (see for example [6]). In one embodiment, the part of MALT1, which is part of the fusion protein, comprises amino acid residues 348-562 of isoform A of MALT1 or the amino acid residues 325-760 of MALT1 of isoform A. The fusion protein may also be a GST-MALT1 fusion protein.

Preferred MALT1 proteins or fusion proteins include BIRC3-MALT1, API2-MALT1 and MALT1-MAP4 described by [5, 6, 7] or a MALT1 fusion protein comprising amino acid residues 339-719 or 339-561 of isotype A of human MALT1 or the corresponding fragment of isotype B of human MALT1.

The first subunit of the diagnostic inhibitor of the present invention is or comprises a detectable label. The expression "detectable label" refers to a subunit of the diagnostic inhibitor, which is detectable and thereby mediates detection of the diagnostic inhibitor or of a complex comprising the diagnostic inhibitor and MALT1. The label may be detectable, for example, by a magnetic property of the label or by absorbing and/or emitting light energy of a specific wavelength or by providing a binding site for a detection agent. An example of a label, which is detectable by emitting light energy of a specific wavelength, is a fluorophore or a chromophore. An example of a label, which provides a binding site for a detection agent is biotin, providing the binding site for avidin and streptavidin. Another example of a detectable label is a sugar or a glycosylated peptide, which can be bound by a lectin. Yet another example of a label is a peptide comprising about six consecutive histidines, which can be bound e.g. to a solid support coated with $Ni^{2+}$.

In one embodiment of the present invention, the detectable label is selected from the group consisting of biotin, glutathione, peptide comprising at least 6 histidines, glycosylated, peptide, metal, metalloprotein, radioisotope, iodine 125 ($^{125}I$), $Co^{2+}$, $Ni^{2+}$, $Cu^{2+}$, and $Zn^{2+}$, chromophore, fluorophore and affinity tag. However, in more general terms, any label detectable by the skilled person may be used.

The second subunit of the diagnostic inhibitor of the present invention is or comprises a peptide, polypeptide or peptidomimetic capable of binding to the catalytic center of activated MALT1.

The term "peptide" as used herein refers to a chain of 4 to 15 amino acid monomers linked by peptide (amide) bonds. The term "chain of 4 to 15 amino acid monomers linked by peptide (amide) bonds" means 4, 5, 6, 7, 8, 9, 10, 11, 12, 13, 14 or 15 amino acid monomers linked by peptide bonds. The term "polypeptide" as used herein refers to a chain of 16 and more amino acid monomers linked by peptide (amide) bonds. The term "polypeptide" also includes proteins of any length.

A "peptide or polypeptide capable of binding to the catalytic center of activated MALT1" refers to any peptide or polypeptide, which can bind to the active site or catalytic center of activated MALT1. Typically, the peptide or polypeptide binds to the substrate recognition site of MALT1 and includes amino acid residues P1, P2, P3 and P4 of a natural substrate of MALT1. Preferably, amino acid residue P1 is the carboxyterminal amino acid of the "peptide" or "polypeptide" of the second subunit.

In one embodiment, the peptide or polypeptide of the second subunit comprises or consists of a tetrapeptide consisting of the amino acid sequence P4-P3-P2-P1, wherein
(i) P4 is selected from C, G, F, I, L, O, V and W;
(ii) P3 is selected from A, E, F, I, L, M O, R, V, W and Y;
(iii) P2 is selected from A, G, I, N, O, P, S and T; and
(iv) P1 is selected from R and Y.

Preferably, P1 of the tetrapeptide is the last amino acid residue (i.e. the carboxyterminal amino acid residue) of the "peptide" or "polypeptide" of the second subunit.

In another embodiment, the second subunit of the diagnostic inhibitor is or comprises a tetrapeptide P4-P3-P2-P1 selected for example from LRSR (SEQ ID No. 5), VRPR (SEQ ID No. 6), LVSR (SEQ ID No. 7), FMSR (SEQ ID No. 8), CLSR (SEQ ID No. 9) and GASR (SEQ ID No. 10). In a preferred embodiment, said second subunit is a peptide comprising or consisting of the amino acid residues ALVSR (SEQ ID No. 11). One or more of the amino acid residues of the second subunit may be replaced by modified amino acids or by molecules mimicking natural amino acids. In other embodiments, the peptide, the tetrapeptide or the polypeptide of the second subunit is replaced by a peptidomimetic. The term "peptidomimetic" as used herein refers to a short peptide-like chain mimicking the peptide, polypeptide or tetrapeptide.

The third subunit of the diagnostic inhibitor of the present invention is or comprises at least one moiety for linking the diagnostic inhibitor to activated MALT1.

The expression "moiety for linking the diagnostic inhibitor to activated MALT1" refers to a chemical entity capable of binding or crosslinking the diagnostic inhibitor to MALT1, wherein binding means covalent binding or non-covalent binding. In more general terms, any chemical entity, which is known by the skilled person to be useful for crosslinking a substrate to the active center of an enzyme, may be used. A moiety for covalently linking the diagnostic inhibitor to MALT1 may be an electrophilic moiety, which covalently binds the diagnostic inhibitor, preferably to the active site cysteine residue of the catalytic center of MALT1. In one embodiment, the moiety is a Michael-Acceptor, such as a substituted methyl ketone, aldehyde, epoxide or aziridine. The moiety may be for example an acyloxymethyl ketone (AOMK), fluoromethylketone (FMK), diazomethylketone, O-acylhydroxylamine, vinyl sulfone, epoxysuccinyl derivate or chloromethlyketone (CMK).

Typically, the moiety defined herein above is covalently linked to the carboxyterminus of the peptide or polypeptide. However, the teaching of the present invention also envisages that the moiety is covalently linked to the diagnostic inhibitor via a linker molecule and/or that the moiety is linked to other parts of the diagnostic inhibitor, for example, to an internal amino acid residue of the peptide or polypeptide of the second subunit.

In one embodiment, the subunits of the diagnostic inhibitor are directly linked to each other. In another embodiment, the subunits are indirectly linked to each other via a rigid or flexible linker molecule positioned between first and the second subunit and/or between the second and the third subunit of the diagnostic inhibitor. The linker may be a short organic molecule such as hexynoyl, pentanoyl, AcLys.

In one embodiment, the first subunit of the diagnostic inhibitor is covalently linked to the second subunit of the diagnostic inhibitor and the second subunit is linked to the third subunit, i.e. the diagnostic inhibitor is characterized by the subunit order: subunit 1-subunit 2-subunit 3. Preferably, subunit 1 is linked to the N-terminal amino acid residue of the peptide or polypeptide and subunit 3 is linked to the C-terminal amino acid residue of the peptide or polypeptide of subunit 2. In other embodiments, however, subunit 1 may be linked to subunit 3 or to an internal amino acid residue of subunit 2. Likewise, subunit 3 may be linked to subunit 1 or to the N-terminal amino acid residue of the peptide or polypeptide of subunit 2 or to an internal amino acid residue of the peptide or polypeptide of subunit 2. The same arrangements are envisaged for the peptidomimetic described herein above.

In a preferred embodiment of the present invention, the diagnostic inhibitor is the diagnostic inhibitor obtainable by the methods described in the Examples, i.e. TAMRA-LRSR-AOMK (SEQ ID No. 5), FITC-LRSR-AOMK (SEQ ID No. 5), (BODIPY-FL)-LRSR-AOMK (SEQ ID No. 5), Ac-Lys (biotin)-LRSR-AOMK (SEQ ID No. 5), alkyne-LRSR-AOMK (SEQ ID No. 5), radioisotope-labeled LRSR-AOMK (SEQ ID No. 5), metalloprotein-labeled LRSR-AOMK (SEQ ID No. 5), fluorophore-labeled LRSR-AOMK (SEQ ID No. 5) or iodine125-labeled LRSR-AOMK (SEQ ID No. 5).

In a second aspect, the present invention relates to a method of identifying or detecting activated MALT1 in a test sample, preferably an ex vivo or in vitro method, said method comprising the steps of:

(a) contacting a test sample with a diagnostic inhibitor of MALT1 activity under conditions allowing the formation of a MALT1 complex of said diagnostic inhibitor and activated MALT1; and (b) qualitative and/or quantitative detection of the MALT1 complex by a first detection agent which binds to a first binding site on the MALT1 complex of (a), wherein said diagnostic inhibitor comprises the following covalently linked subunits:

(i) a first subunit comprising at least one detectable label, (ii) a second subunit comprising a peptide or polypeptide capable of binding to the catalytic center of activated MALT1, and (iii) a third subunit comprising at least one moiety for linking the diagnostic inhibitor to activated MALT1.

The method may comprise one or more additional steps, e.g. an additional step of concluding from the detectable amount of MALT1 complex on the amount of activated MALT1 in the sample. Preferably, the detectable amount of MALT1 complex correlates with the amount of activated MALT1 or it is identical with the amount of activated MALT1 or the cleavage of fluorophore substrate such as fluorophore labeled LRSR-AMC.

The expression "ex vivo method" relates to a method that is performed outside of the human or animal body. Typically, an ex vivo method is performed on a test sample obtained from an animal or a human subject.

The expression "activated MALT1" as used herein refers to MALT1 in its active state. A MALT1 in the active state, as defined herein, has MALT1 activity, i.e. it is capable of binding to a native substrate of human MALT1, for example to BCL10, A20, CYLD, RelB or Regnase or to the tetrapeptide or pentapeptide described herein. Active MALT1 can be distinguished from inactive MALT1 for example by the ability to bind any of the aforementioned substrates or by the ability to proteolytically cleave a MALT1 substrate. Binding of a substrate to activated MALT1 can be established for example by co-immunoprecipitation of MALT1 and substrate, and protease activity can be established by determining the presence or amount of one or more proteolytic fragments of the substrate.

Preferably, MALT1 activity is determined in a MALT1 cleavage assay. Preferably, 200 ng GST-MALT1 or a comparable amount of the MALT1 polypeptide described herein is incubated together with 1 mM Ac-LRSR-AMC (7-Amino-4-methylcoumarin), HA-MALT1 wt or mutant substrate for 2 h at 30° C. The assay may be performed in cleavage buffer comprising for example 50 mM MES, 1 M sodium citrate pH 7, 150 mM NaCl, 10% sucrose, 0.1% chaps, 10 mM DTT. Catalytically active MALT1 cleaves the substrate and an increase of AMC fluorescence can be measured.

The expression "test sample" refers to a sample of a human or animal subject used for performing the method of the present invention. The test sample may be obtained from blood, serum, bone marrow, sputum, bronchial lavage, bodily secretions, somatic or non-somatic tissue and is, preferably, a sample, which is either suspected of being characterized by comprising an increased amount of activated MALT1 or a sample which is suspected of being characterized by an increased MALT1 activity. The "test sample" may also comprise buffer or any other reagent, which is, for example, used for performing the method of the present invention. The expression "MALT1 activity" is an activity, preferably the proteolytic activity, resulting from activated MALT1 including any of the aforementioned MALT1 polypeptides.

According to the teaching of the present invention, a test sample is characterized by an increased amount of activated MALT1 if, in comparison to a reference sample or in comparison to a tissue-specific reference amount of activated MALT1, an increased amount of activated MALT1 is detected, wherein the reference sample and the tissue-specific reference amount is derived from healthy tissue and/or from a healthy subject. The test sample and the reference sample are preferably obtained from a corresponding source (blood, tissue, liquid, bone, lymph node . . . ). The amount of activated MALT1 detected in a reference tissue sample may be used for calculating a tissue-specific reference amount. The term "tissue-specific reference amount" also encompasses liquid samples such as a blood sample or a sample comprising interstitial liquid and refers to an average or standard amount of activated MALT1 typically observed in a specific healthy tissue or in a specific compartment of the body. The information relating to tissue-specific reference amount may be stored on or provided by a database. The tissue-specific reference amount of activated MALT1 may be a mathematical expression reflecting the absolute amount of activated MALT1 or an amount of activated MALT1 normalized with respect to the sample volume (e.g. µg of tissue) or with respect to the amount of an internal standard such as a biomarker. The internal standard or biomarker may be, for example, the amount of a protein such as β-actin or total MALT1, or the amount of a phospholipid, DNA, RNA or the like. In some embodiments, the amount of internal standard or biomarker may be the total amount of MALT1 in the sample or the amount of inactive MALT1.

The expression "contacting a test sample with a diagnostic inhibitor of MALT1 activity" means bringing the test sample in contact with the diagnostic inhibitor of the present invention. The test sample may be brought in contact with the diagnostic inhibitor, for example, by adding and/or mixing the diagnostic inhibitor to the test sample. The diagnostic inhibitor may be immobilized, for example by covalently or non-covalently linking the diagnostic inhibitor to a solid support. In more general terms, solid support may be any kind of carrier known to the skilled person as carrier for immobilizing molecules. For example, the diagnostic inhibitor may be attached to a microtiter plate (also microplate) or to beads or particles, such as gold beads or gold particles. Thus, the test sample may be contacted with the diagnostic inhibitor by incubating an inhibitor coated microtiter plate or beads with the test sample. Examples of beads are acceptor beads, gold beads or streptavidin beads.

The expression "diagnostic inhibitor of MALT1 activity" relates to the diagnostic inhibitor of the present invention, which is described in more detail above. This diagnostic inhibitor is a detectably labeled compound that is capable of forming a complex with MALT1 by binding to activated MALT1 and that is capable of inhibiting MALT1. Inhibiting MALT1 means preventing substrate binding and/or preventing proteolytic activity of the MALT1 polypeptide. Preferably, the diagnostic inhibitor of the present invention is specific or selective for MALT1 and/or binds selectively to activated MALT1. Preferably, selective binding to activated MALT1 means that the diagnostic inhibitor does not bind to proteolytically inactive MALT1.

The expression "MALT1 complex" refers to a stable structure formed by binding of the diagnostic inhibitor of the present invention to activated MALT1. The MALT1 complex thus comprises at least MALT1 and the diagnostic inhibitor of the present invention, which may be linked by a covalent or non-covalent interaction. Additional binding partners of MALT1, such as cellular proteins, may also be comprised in said MALT1 complex.

The expression "conditions allowing the formation of a MALT1 complex of said diagnostic inhibitor and activated MALT1" refers to the conditions of incubation, which affect the formation of the complex between the diagnostic inhibitor and activated MALT1. Incubation conditions mean concentration of diagnostic inhibitor, time of incubation, buffer and salt conditions, temperature and the like. For example, incubation in a physiological buffer such as hepes pH 7.4 or PBS is suitable for forming the MALT1 complex with the diagnostic inhibitor of the present invention. The examples illustrating the present invention describe preferred conditions for forming the MALT1 complex of the present invention.

The expression "qualitative detection of activated MALT1" or "qualitative detection of the MALT1 complex" means determining the presence or absence of active MALT1 and may comprise establishing the identity of the activated MALT1, e.g. by determining the amino acid sequence of said MALT1 or by determining its antigenicity, for example by analyzing binding of antibodies which selectively bind to specific variants of MALT1. Determining the presence or absence preferably refers to the detectable presence or absence of MALT1, which may vary due to detection limits and which may be less than the entire amount of MALT1 of the sample. Preferably, detectable amount means at least 50%, 60%, 70%, 80%, 90%, 95%, 96%, 97%, 98%, 99% or 100% of MALT1 of the sample.

The expression "quantitative detection of activated MALT1" or "quantitative detection of the MALT1 complex" means determining the amount of MALT1 complex and concluding on the amount of active MALT1. Determining the amount may comprise determining a concentration, an absolute amount or a relative amount of activated MALT1 or of MALT1 complex. The relative amount may be determined with respect to a reference marker such as a reference biomarker.

In one embodiment, the amount is determined by (a) performing the method of the present invention on a test sample and on one or more reference samples with defined amounts of activated MALT1 and by (b) comparing the amount of activated MALT1 detectable in the test sample, with the amount of activated MALT1 detectable in the reference samples. Preferably, the reference sample is preincubated with the diagnostic inhibitor of the present invention. This embodiment may comprise a step of concluding from the comparison on the amount of active MALT1 present in the test sample.

The expression "first detection agent which binds to a first binding site on the MALT1 complex" relates to an agent, which is used for detection of the MALT1 complex. In one embodiment, the binding site of the first detection agent is located on MALT1. In another embodiment, the binding site of the first detection agent is located on the diagnostic inhibitor.

In one embodiment of the present invention, the first detection agent is specific for the diagnostic inhibitor. Preferably, the first detection agent binds to the first subunit of the diagnostic inhibitor, i.e. to the detectable label. In other words, the first detection agent is a binding partner of the detectable label of the diagnostic inhibitor.

In principle, the detectable label may be detected by any suitable method of detection known to the skilled person. Thus, the first detection agent may be, for example, streptavidin and the detectable label of the diagnostic inhibitor may be biotin. The binding partners may also be reversed such that the first detection agent may be biotin and the detectable label of the diagnostic inhibitor may be streptavidin. It is evident for the skilled person that any two binding partners may replace the binding partners biotin/streptavidin. For example, the first detection agent may be $Ni^{2+}$ and the detectable label of the diagnostic inhibitor may be a histidine hexapeptide. The first detection agent may be soluble or in suspension or it may be bound to a solid support such as a microtiter plate or spherical beads.

In one embodiment, the present invention's method of detection comprises a step of isolating the MALT1 complex, i.e. separating the MALT1 complex from MALT1 which did not react with the diagnostic inhibitor. This MALT1 complex comprising MALT1 and the diagnostic inhibitor of the present invention may be isolated for example by bringing a test sample comprising MALT1 complex and MALT1 not bound to the diagnostic inhibitor, in contact with the first detection agent under conditions allowing the formation of a complex comprising said MALT1 complex and the first detection agent. Said first detection agent may be bound to a solid support. For example, the test sample comprising MALT1 complex and MALT1 not bound to the diagnostic inhibitor may be incubated on a microtiter plate coated with the first detection agent. MALT1 not bound to the diagnostic inhibitor may be washed away from said MALT1 complex.

In one embodiment, the qualitative and/or quantitative detection of activated MALT1 or of the MALT1 complex comprises detection by a second detection agent that binds, preferably specifically, to a second binding site on the MALT1 complex. Preferably the second detection agent is specific for MALT1 so that it functions as an enhancer of detection of the MALT1 complex. The second detection agent may bind to any second binding site on the MALT1 complex, which is different from the first binding site of the first detection agent. The second detection agent may be an antibody binding to the MALT1 polypeptide. Alternatively, the second detection agent may be a binding partner of activated MALT1 or of the MALT1 polypeptide described herein above or it may be a functional part of the binding partner, which is capable of interacting with MALT1 or the MALT1 polypeptide. Preferably, the binding partner is BCL10 or CARMA1.

Alternatively, the second detection agent is an antibody specific for MALT1.

As used herein, the term "antibody" refers to polyclonal and monoclonal antibodies and to antibody derivatives such as chimeric or humanized antibodies or antigen binding fragments of antibodies. Comprised are Fab fragments such as F(ab')2, Fab, Fv, and Fd fragments of antibodies, chimeric antibodies, in which the Fc and/or FR and/or CDR1 and/or CDR2 and/or light chain-CDR3 regions have been replaced with homologous human or nonhuman sequences, chimeric F(ab')2-fragment antibodies in which the FR and/or CDR1 and/or CDR2 and/or light chain-CDR3 regions have been replaced with homologous human or nonhuman sequences, chimeric Fab-fragment antibodies in which the FR and/or CDR1 and/or CDR2 and/or light chain-CDR3 regions have been replaced with homologous human or nonhuman sequences, and chimeric Fd-fragment antibodies in which the FR and/or CDR1 and/or CDR2 regions have been replaced with homologous human or nonhuman sequences. The term "antibody" also comprises "single-chain" antibodies.

In an embodiment of the present invention, the second detection agent comprises an antibody or antigen binding fragment thereof, preferably a MALT1 antibody, and a detectable label. Preferably, the detectable label of the second detection agent is coupled to the MALT1 antibody or to the antigen binding fragment or to a secondary antibody, which is capable of binding to said MALT1 antibody. Alternatively, the detectably labeled secondary antibody may be added separately, i.e. after binding of the unlabeled second detection agent. The secondary antibody may be for example a monoclonal or a polyclonal antibody or any of the antibody fragments or derivatives described herein above.

The detectable label may be selected from, for example, chemiluminescence labels, enzyme labels and fluorescent labels. The fluorescent label may be, for example, Texas-Red, fluorescein isothiocyanate (FITC), rhodamine, rhodamine derivative, fluorescein, fluorescein derivative, cascade blue, Cy5 and phycoerythrin.

In another embodiment, the first detection agent is linked or coupled to a solid support. The solid support may be for example a microtiter plate, agarose or polyacrylamide beads, gold beads and the like, magnetic beads, latex beads, nanoparticles, macro-beads, membranes, microplates, array surfaces, dipsticks.

In another embodiment, the first detection agent is selected from the group consisting of avidin, streptavidin, StrepTactin, HA, FLAG, GST or functional fragment of GST, peptide comprising at least 6 histidines, lectin, antibody capable of binding to the detectable label.

The teaching of the present invention also envisages normalizing the amount of activated MALT1 or the amount of MALT1 complex determined or identified in a sample. Normalization may be used for adjusting sample sizes or signal intensities. Thus, the present invention may comprise a step of determining the amount of sample volume (e.g. µg of tissue) or the amount of an internal standard such as a reference biomarker. The method of the present invention may also comprise a step of determining the ratio of amount of activated MALT1 or amount of MALT1 complex to the amount of a reference biomarker. The biomarker may be, for example, a protein such as β-actin, phospholipid, DNA, RNA or the like. In some embodiments, the amount of biomarker may be the overall amount of MALT1 or the amount of inactive MALT1 detectable in the sample. For example, the method of the present invention may also comprise a step of determining the amount of inactive MALT1 in the sample and a step of determining the ratio of amount of activated MALT1 to amount of inactive MALT1. The amount of inactive MALT1 in a sample may be established for example by removing the MALT1 complexes from the sample and by subsequently determining the amount of MALT1 remaining in the sample. The remaining MALT1 in the sample is considered as inactive MALT1, its amount may be determined by using conventional immunological assays, for example by using a quantitative ELISA specific for MALT1.

Quantitative sample information specifying the amount of activated MALT1, the sample size and/or the amount of biomarker, the ratio of amount of activated MALT1 to the sample size or to the amount of biomarker, can be stored in a database or on a computer. This quantitative information may be linked to information specifying the source of the tissue of the sample.

Accordingly, in another aspect the present invention relates to a database, comprising information relating to the (a) amount of activated MALT1, (b) amount of a biomarker and/or ratio of activated MALT1 to sample size or to the amount of biomarker; and/or (c) tissue source.

In another aspect, the present invention relates to a method of detecting or diagnosing a disease or a predisposition for developing a disease, preferably an ex vivo or in vitro method, said disease being characterized by an increased amount of MALT1 or by an increased MALT1 activity, said method comprising the steps of:

(a) contacting a test sample and a reference sample with the diagnostic inhibitor of the present invention under conditions allowing the formation of a MALT1 complex of said diagnostic inhibitor and activated MALT1;

(b) qualitative and/or quantitative detection of the MALT1 complex in the test sample and the reference sample; and (c) concluding from the observation of an increased amount of MALT1 complex in the test sample that the subject is affected from the disease or has a predisposition for the disease.

The expression "disease" or "disease characterized by an in increased MALT1 activity" refers to any pathological condition, which is associated with cells or tissue characterized by an increased amount of activated MALT1 or cells or tissue showing an increased MALT1 activity. According to the teaching of the present invention, the disease is preferably a tumor or cancer disease, an autoimmune disease or an inflammatory disease, such as multiple sclerosis, rheumatoid arthritis or a lymphoma, or MALT lymphoma or a diffuse large B-cell lymphoma of the subtype ABC-DLBCL or a mantle cell lymphoma.

The expression "reference sample" as used herein refers to a control sample comprising cells and tissue not affected from a disease characterized by an increased MALT1 activity or an increased amount of activated MALT1. The reference sample may be obtained from healthy tissue of the subject affected from the disease or it may be obtained from a healthy reference subject known to be free of the disease.

The step of comparing the amounts of activated MALT1 in the test sample and in the reference sample also encompasses a comparison with the amount of activated MALT1 of a reference sample stored in a database or on a computer, including the tissue-specific reference amount described herein above.

The information resulting from any of the methods described herein may be used for screening a group of cancer patients for individual subjects responsive or sensitive to a therapy with a therapeutic MALT1 inhibitor. In other words, the methods of the present invention may be used for identifying or selecting patients amenable to a therapy with a therapeutic MALT1 inhibitor.

Thus, in another aspect, the present invention relates to a method for detecting the response or sensitivity of activated MALT1 to a therapeutic agent capable of inhibiting MALT1 activity, preferably an ex vivo or in vitro method, the method comprising the steps of:

(a) qualitative and/or quantitative detection of activated MALT1 of a test sample and of a reference sample by performing the method of detection of the present invention described herein above, wherein the test sample is pre-incubated with a therapeutic agent capable of inhibiting MALT1 activity;

(b) comparing the amount of activated MALT1 in the test and the reference sample; and (c) concluding from a reduced detectable amount of activated MALT1 in the test sample that the subject is sensitive to the therapeutic agent.

The term "detecting the response or sensitivity of activated MALT1 to a therapeutic agent" means establishing as to whether or not the MALT1 activity observed in cells and/or tissue of a subject can be reduced by treating the subject or the cells and/or tissue of the subject with the therapeutic agent.

The term "therapeutic agent capable of inhibiting MALT1 activity" refers to any agent which reduces MALT1 activity. MALT1 activity may be reduced by reducing the level of RNA encoding MALT1 polypeptides, for example, by using siRNA or antisense nucleic acids specific for Malt1. Alternatively, MALT1 activity may be reduced by reducing the catalytic activity of MALT1, for example by using inhibitors binding to MALT1 and, thus, preventing the proteolytic cleavage of substrate into product. According to the teaching of the present invention, any of the known paracaspase inhibitors such as z-VRPR-FMK (SEQ ID No. 6), LRSR-AOMK (SEQ ID No. 5) and LRSR-FMK (SEQ ID No. 5) may be considered as therapeutic agent. Preferably, the therapeutic agent is selective for MALT1. Alternatively, however the therapeutic agent capable of inhibiting MALT1 activity is an agent modifying the amount or activity of a component upstream of MALT1, such as BTK inhibitor Ibrutinib. The therapeutic agent capable of inhibiting MALT1 activity may be for example promazine (N,N-dimethyl-1-(10H-phenothiazin-10-yl)propan-2-amine), thioridazine (10-[2-(1-methylpiperidin-2-yl)ethyl]-2-(methylthio)phenothiazine), MI-2 [23,29] or mepazine (10-[(1-methylpiperidin-3-yl)methyl]-10H-phenothiazine) or a phenothiazine derivative. Preferably, the therapeutic MALT1 inhibitor is 10-{[(3S)-1-methylpiperidin-3-yl]methyl}-10H-phenothiazine, the (S)-enantiomer of mepazine ("(S-)mepazine").

The term "pre-incubated with a therapeutic agent" means that before MALT1 is exposed to the diagnostic inhibitor of the present invention, it is exposed to the therapeutic agent described herein, preferably under conditions suitable for inhibiting MALT1 activity. Suitable incubation conditions refer to the concentration of therapeutic agent, time of incubation, buffer and salt conditions, temperature and the like. For example, incubation in a physiological buffer such as hepes pH 7.4 or PBS is suitable for inhibiting MALT1 activity.

In another aspect, the present invention relates to a method for monitoring a subject's sensitivity or response to a medication for treating a disease characterized by an increased MALT1 activity, comprising the steps of:

(a) qualitative and/or quantitative detection of activated MALT1 of a test sample and of a reference sample by performing the method of detection of the present invention described herein above, wherein the test sample is a sample obtained from the subject after treatment of the subject with a therapeutic agent and the reference sample is a sample obtained prior to the test sample, preferably before treatment of the subject with the therapeutic agent;

(b) comparing the amount of activated MALT1 in the test sample and the reference sample; and (c) concluding whether the subject is sensitive or has responded to the therapeutic agent or concluding from a reduced detectable amount of activated MALT1 in the test sample in comparison with the reference sample whether the therapeutic agent effects a MALT1 response.

As explained herein above, the term "therapeutic agent" refers to any therapeutically active compound capable of reducing the amount or activity of MALT1 and includes, for example, siRNA, which is specific for MALT1 or upstream inhibitors of MALT1 such as Bruton Tyrosine Kinase (BTK) inhibitors Ibrutinib/PCI-32765 (Pharmacyclics), VL-101 and AVL-291 (Avila Therapeutics), Dasatinib/Sprycel, Phosphoinositide 3-kinase inhibitors (PI3K inhibitor), a Protein Kinase C (PKC) 13 inhibitor such as Sotrastaurin (STN) or any of the therapeutic agents described herein.

Thus, the teaching of the present invention also provides a method for monitoring the course of a disease during treatment with a therapeutic agent, which method includes determining regression or progression of the disease. Typically, during treatment of the disease with a therapeutic agent, a first sample is obtained as a reference sample and a second sample is obtained as a test sample.

According to the teaching of the present invention, the first sample, i.e. the reference sample, may be obtained prior to or during therapy with the therapeutic agent. The second sample, i.e. the test sample, is preferably obtained during or after treatment with the therapeutic agent, wherein the first sample is obtained prior to the second sample. Preferably, the first sample is obtained at a first point in time and the second sample is obtained at a second point in time, wherein the first point in time is separated from the second point in time by at least 1, 2, 3, 4, 5, 6, 7, 8, 9, 10, 11, 12, 13, 14, 15, 16, 17, 18, 19, 20, 21, 22, 23 or 24 hours, days, weeks or years.

A reduced detectable amount of activated MALT1 in the test sample allows the conclusion that the subject is sensitive or has responded to the therapeutic agent. The expression "reduced detectable amount" preferably means that the amount of activated MALT1 in the test sample is reduced with respect to the reference sample by more than 5%, 10%, 15%, or more than 20%.

An increased or identical detectable amount of activated MALT1 in the test sample and the reference sample allows the conclusion that the subject has essentially not responded to the therapeutic agent. The expression "increased or identical detectable amount" preferably means that the amount of activated MALT1 in the test sample corresponds to the amount of detectable MALT1 in the reference sample or exceeds the amount in the reference sample by at least 5%, 10% 20%, 15%, 10%, 20% or at least 30%.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used for targeting and degrading mRNA encoding a MALT1 polypeptide. A range of 19-25 nucleotides is the most preferred size for siRNAs. As an example, the siRNA is or comprises the nucleotide sequence 5'-UCACUGU-GUUACUGGAUGA-3' (SEQ ID No. 13).

In another aspect, the present invention also relates to the use of the diagnostic inhibitor of the present invention for the preparation of a composition for diagnosing a disease or a predisposition to a disease, said disease being characterized by an increased MALT1 activity or a requirement for MALT1 activity.

In another aspect, the present invention also relates to the use of the diagnostic inhibitor of the present invention for diagnosing a disease or a predisposition to a disease, said disease being characterized by an increased MALT1 activity or a requirement for MALT1 activity.

In yet another aspect, the present invention relates to a kit for performing the method the present invention, wherein said kit comprises: (i) the diagnostic inhibitor of the present invention and/or a therapeutic agent capable of reducing MALT1 activity and/or (iii) instructions for use. The instructions for use comprise, for example, a description of any of the methods of the present invention.

The invention is illustrated by the following examples, which are not to be construed to limit the present invention in any way.

EXAMPLES

Example 1: Materials and Methods

Antibodies, Reagents and Plasmids

The following antibodies were used: MALT1 (B12), β-Actin (I19) (all Santa Cruz Biotechnology); Flag-M2 (Sigma); Carmal (1D12) and MALT1 (2494; ELISA) (both Cell Signaling); A20 (eBioscience). The following reagents were used: z-VRPR-FMK (Alexis Biochemicals) (SEQ ID No. 6), mepazine, thioridazine (both ChemBridge), CA-074Me and CA-074 (Calbiochem), Ac-LRSR-AMC (SEQ ID No. 5) and DEVD-AMC (both Peptides International) (SEQ ID No. 12), zRR-AMC (Millipore), Protein G Sepharose (PGS, GE Healthcare), TMB substrate solution (eBioscience). Human cathepsin B and caspase-8 (BioVision). Streptavidin Agarose Resin (Thermo Scientific), Streptavidin coated plates (high binding) (Thermo Scientific). Reagents for chemical synthesis: 2-chlorotrityl chloride resin (Merck), Fmoc-Arg(Pbf)-OH, Fmoc-Ser(t-Bu)-OH, Fmoc-Leu-OH (all Creosalus), 5-hexynoic acid, diazald, isobutyl chloroformate, N-methylmorpholine, potassium fluoride, dimethyl benzoic acid, fluorescein-isothiocyanate (all Sigma-Aldrich). N-terminal FLAG-A20 constructs, N-terminal FLAG- (or HA-) MALT1 wt and active site mutant constructs were cloned in the pEF backbone vector (Invitrogen) (in overexpression experiments, MALT1 Isoform B was used with active site mutation C453A, which corresponds to C464 in Isoform A; for clarity, we used C464 in figure descriptions). siRNAs from Eurogentec: control siGFP, siMALT1: UCACUGUGUUACUG-GAUGA (SEQ ID No. 13).

Chemical Synthesis of Diagnostic MALT1 Inhibitors

For the synthesis of the AOMK-based diagnostic MALT1 inhibitors, we first used a combined solid phase/solution phase synthesis, which constructs the peptide recognition element on a chlorotrityl resin and installs the dimethyl benzoic acid leaving group in the final steps (FIG. 1, Scheme 1a) [8]. Although this yielded the desired probe 2 (0.67 mg, 1.7% yield; ESI-MS: [M+H]$^+$ 771.4494 (found), 771.4512 (calculated); [M+2H]$^{2+}$ 386.2358 (found), 386.2293 (calculated) (data not shown), a significant amount of the hydroxylmethyl ketone (the hydrolysis of the intermediate diazomethyl ketone and chloromethyl ketone) was formed. We next followed a solid phase protocol reported by Kato et al (FIG. 1, Scheme 1b) [26]. In brief, resin-bound intermediate 3 was elongated with 5% diethyl amine (DEA) in DMF for Fmoc deprotection, followed by a DIC/HOBt-mediated amino acid coupling. After final capping of the N-terminus with FITC, the probe was cleaved from the resin and analyzed by LC-MS. Unfortunately, the dimethyl benzoic acid group of the AOMK electrophile was substituted by DEA. Displacement of the acyloxy group of AOMKs by nitrogen bases was a problem, repeated Fmoc-deprotection by DEA is apparently not compatible with the dimethylbenzoic acid group. To facilitate a successful solid phase synthesis, we used 0.1 M tetrabutylammonium fluoride (TBAF) to deprotect the Fmoc-group [33]. Under these conditions, the dimethyl benzoyl group is stable. During the first attempt using this synthesis route, we noticed that cleavage from the resin directly followed by HPLC purification led to a contamination of the probe with tetrabutylammonium ions. Hence, after final Fmoc-deprotection, we extensively washed the resin with MeOH, DMF and DCM, then cleaved the AOMK from the resin and precipitated it in cold ether. For probes 5 and 6, we then reacted the precipitate with FITC (1.1 eq) or BODIPY-FL, succinimidyl ester (1.1 eq), and DIEA (3 eq) in DMSO. After 2 h, the reaction mixture was purified by RP-HPLC (20-60% gradient of acetonitrile in water+ 0.1% TFA), yielding probes 5 (7.6%), 6 (3.5%) and 7 (1.9; yields based on Fmoc-loading of resin 3); ESI-MS: 5: [M+2H]$^{2+}$ 533.7241 (found), 533.7262 (calculated), [M+3H]$^{3+}$ 356.1528 (found), 356.1532 (calculated). 6: [M+4]$^+$ 951.5120 (found), 951.5182 (calculated), [M+2H]$^{2+}$ 476.2594 (found), 476.2628 (calculated) 7: [M+H]$^+$ 1073.5776 (found), 1079.5924 (calculated), [M+2H]$^{2+}$ 537.2920 (found), 537.2999 (calculated), [M+3H]$^{3+}$ 358.5308 (found), 358.5356 (calculated) (data not shown).

Click Chemistry

Copper I-catalysed click chemistry reaction was performed in 50 μl 50 mM hepes with 10 μM alkyne-LRSR-AOMK (probe 2) and 10 μM N-TAMRA-3-aminopropylazide or 100 µM N-FITC-3-aminopropylazide. Reducing agent sodium ascorbate (0.5 mM), TBTA (50 µM) and CuSO$_4$ (1 mM) were added to the reaction and incubated for 45 min at RT.

Cloning, Expression and Purification

For preparing MALT1 complex with peptidic inhibitor, human MALT1 (L339-R719) was expressed in *Escherichia coli* Rosetta™ (DE3) strain (Novagen). Cells were resuspended in lysis buffer (50 mM hepes pH=7.5, 300 mM NaCl, 7 mM imidazol and 4 mM (3-mercaptoethanol), lysed by sonication and clarified by centrifugation. Proteins were further purified by Ni-NTA affinity chromatography (Qiagen) and size exclusion chromatography (S200 26/60, GE-Healthcare). Monomeric and ligand free dimeric MALT1 elute as single peak in size-exclusion-buffer (25 mM hepes pH=7.5, 300 mM NaCl, 5 mM DTT) and were concentrated to 8 mg/ml. Monomeric MALT1 was incubated with three-fold molar excess of the peptide inhibitors at 10° C. overnight. After additional size exclusion chromatography (S200 16/60 GE-Healthcare) dimeric MALT1 bound to the tetrapeptide inhibitors was concentrated to 6 mg/ml.

Caspase 8 and Cathepsin B Cleavage Assay 0.1 Unit recombinant Caspase-8 together with probe 5 and z-VRPR-FMK (SEQ ID No. 6) was incubated with 1 mM DEVD-AMC (SEQ ID No. 12) substrate. The same experimental conditions from the MALT1 cleavage assay were used.

0.2 ng cathepsin B together with probe 5, z-VRPR-FMK (SEQ ID No. 6), mepazine or CA-074 was incubated with 1 mM zRR-AMC substrate for 2 h at 30° C. Assay was performed in 0.1 M sodium acetate pH 5.5, 10 mM DTT and 0.1 mM EDTA. Again, increase of AMC fluorescence is measured in a Synergy 2 Microplate Reader (Biotek).

Cell Culture

Jurkat T cells were cultured in standard RPMI medium containing 10% FCS, 100 U/ml Penicillin/Streptomycin and 2 mM Glutamin. DNA transfection of 6 µg DNA in 8×10$^6$ Jurkat T cells was performed by electroporation in a GenePulser Xcell (BioRad) with a 220 Volt pulse. For siRNA experiments, Jurkat T cells were transfected with 100 nM siRNA and Atufect transfection reagent (Silence Therapeutics, Berlin). Jurkat T cells were stimulated either with 200 ng/ml PMA (phorbol 12-myristate 13-acetate) and 300 ng/ml Ionomycin (both Calbiochem) or CD3/CD28 antibody co-ligation (human CD3: 1 µg/ml; human CD28: 4 µg/ml; mouse IgG1: 2 µg/ml; mouse IgG2a: 2 µg/ml; BD Biosciences). DLBCL cell lines (HBL1, TMD8, OCI-Ly3, U2932, RIVA, BJAB, Su-DHL-4 and Su-DHL-6) were cultured in standard RPMI medium containing 20% FCS, 100 U/ml Penicillin/Streptomycin and 2 mM Glutamin. OCI-Ly10 cell line was cultured in IMDM containing 20% human serum, 100 U/ml Penicillin/Streptomycin, 2 U/ml heparine, 50 µM β-mercaptoethanol. Inhibitors 10 µM (z-VRPR-FMK, Mepazine, Thioridazine, CA-074Me) were added to the cells in media for 1 h, prior to stimulation and labeling with diagnostic MALT1 inhibitor. The cellular MALT1 assay of Example 6 was performed at the inhibitor concentrations indicated in FIG. 9.

Purification of Primary Human PBMCs and T Cells

Human blood was treated with heparine (16 U/ml) and centrifuged (300×g 10 min RT) to create the buffy coat; intermediate cell layer was transferred and purification of cells was performed according to the Dynabeads Untouched Human T cell Kit (Invitrogen).

Informed consent was obtained from donors of human blood.

Labeling with Diagnostic MALT1 Inhibitor after Immunoprecipitation (IP)

Cells were lysed in 500 µl co-IP buffer without protease inhibitors (25 mM hepes pH 7.5, 150 mM NaCl, 0.2% NP-40, 10% glycerol, 1 mM DTT, 10 mM sodium fluoride, 8 mM (3-glycerophosphate and 300 µM sodium vanadate), centrifuged (14000 rpm, 10 min, 4° C.) and overexpressed FLAG MALT1 was immunoprecipitated by FLAG (M2) antibody for 3 hours at 4° C. PGS was added for 1 h at 4° C., precipitate was washed 2× with co-IP buffer and 1× with 50 mM hepes pH 7.4. Precipitated MALT1 was incubated with 0.3 µM pre-clicked probe 2 (in 20 µl 50 mM hepes pH 7.4) for 50 min at 29° C., mixed with 4× loading dye and boiled for 3 min. After protein separation by SDS PAGE, staining with diagnostic inhibitor was detected by Typhoon Fluorescence Scanner (FITC laser 488 nm/filter 526 SP; TAMRA laser 532 nm/filter 580 BP).

Labeling with Diagnostic Inhibitor in Cell Extracts

Jurkat T cells (1-2×10$^7$), primary human PBMCs or primary human T cells (0.25 or 1×10$^7$) were lysed in 150 µl co-IP buffer without protease inhibitors. DLBCL (3×10$^7$) were lysed in 250 µl buffer. After centrifugation (14000 rpm, 10 min, 4° C.), 100 µl extract (DLBCL: 200 µl) was stained with probe 5 or probe 6 (3 µM end) for 50 min at 29° C., mixed with 4× loading dye and boiled.

Inhibitor-Labeling in Probe 7-Pulldown

Untreated DLBCL (1-2×10$^7$) or Jurkat T cells (stimulated with PMA/Ionomycin or CD3/28 or left untreated; 1-2×10$^7$), were lysed in 500 µl co-IP buffer without protease inhibitors, centrifuged, incubated with probe 7 (concentration as depicted) for 1 h at RT then incubated with streptavidin beads for 2 h at 4° C. Precipitate was washed, analysed by SDS-PAGE and western blot.

ELISA-Based Assay

Untreated DLBCL (1×10$^7$), primary T cells (0.25×10$^7$) or Jurkat T cells (0.2-1×10$^7$) (stimulated or not) were lysed in 300 µl co-IP buffer without protease inhibitors, centrifuged, incubated with probe 7 (concentration as depicted) for 1 h at RT, then transferred to streptavidin-coated plates (96 well, clear) and incubated o/n at 4° C. After blocking with 2% BSA in PBS-T, detection was performed by incubation with MALT1 primary antibody (1 h, RT) and HRP-coupled secondary antibody (1 h, RT). Luminescence was determined after TMB substrate incubation in a photometer (Bio-Tek).

Example 2: Design of the Diagnostic MALT1 Inhibitor

Design and Synthesis

Figure 1:
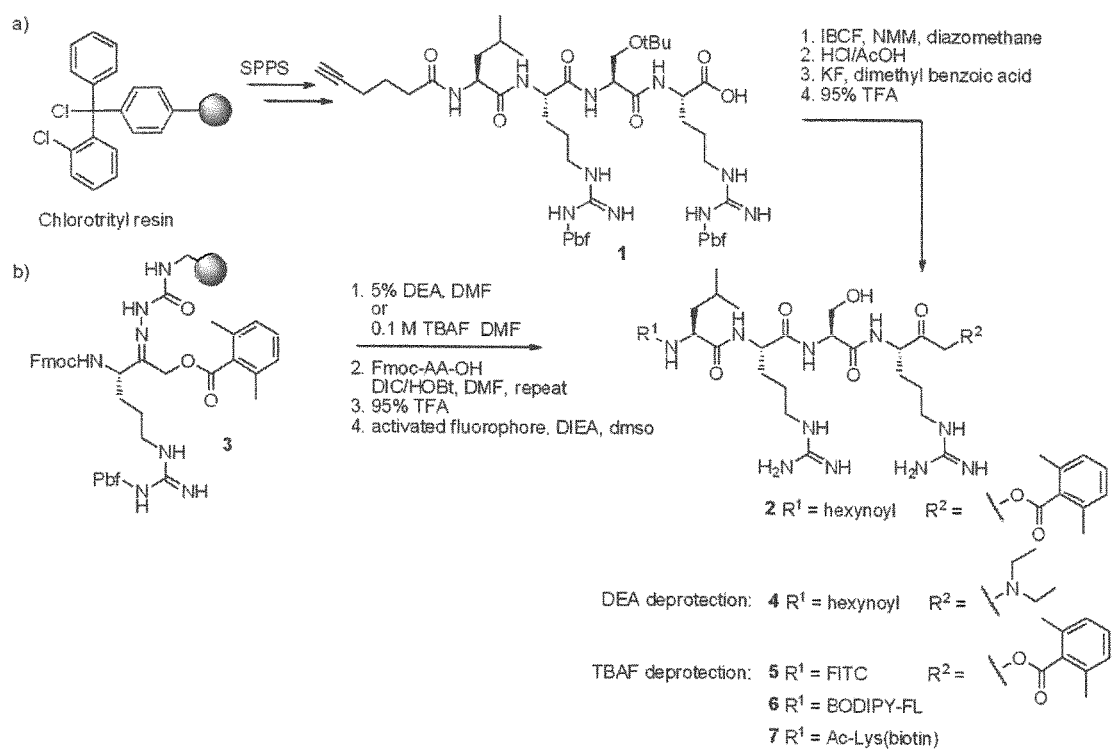
FIG. 1: Synthesis of AOMK probes 2 and 5-7 (scheme 1).
a) Construction of the tetrapeptide part on chlorotrityl resin followed by AOMK installation in solution.
b) Solid phase synthesis of the probe on resin starting from bound AOMK building block.

We based the design of our diagnostic MALT1 inhibitor on the acyloxymethyl ketone (AOMK) electrophile because of its high specificity for cysteine proteases and low background signals [26, 1-3]. As specific recognition element we chose the tetrapeptide sequence LRSR (SEQ ID No. 5) derived from the cleavage site of BCL10, one of the best MALT1 substrate sites [12]. As detectable label, we introduced either a fluorescein, BODIPY-FL, biotin or an alkyne. The latter is amenable for tandem labeling by click chemistry [27]. For the synthesis of these probes, we followed two strategies [8, 1-3]. In the first route the peptide part was constructed on a chlorotrityl resin (FIG. 1, Scheme 1a). After cleavage, the C-terminal carboxylic acid was subsequently converted into an AOMK by a three step sequence. Although this route yielded the desired product 2, it gave rise to the formation of the hydroxymethyl ketone as a by-product. In a second synthetic approach (FIG. 1, Scheme 1b), we first attached the arginine AOMK building block to the solid phase through a hydrazone linkage (compound 3) and then elongated the peptide as described [1-3]. Unfortunately, the AOMK is prone to substitution by amines, and repeated exposure to diethylamine during Fmoc-deprotection led to full conversion to 4. As an alternative, we used a 0.1M TBAF solution for the deprotection of the Fmoc-group, which kept the AOMK intact and led to the successful isolation of the diagnostic MALT1 inhibitors 5, 6 and 7.

Example 3: FITC-Detection of MALT1 Inhibitor Complexes in T Cells

Figure 2:
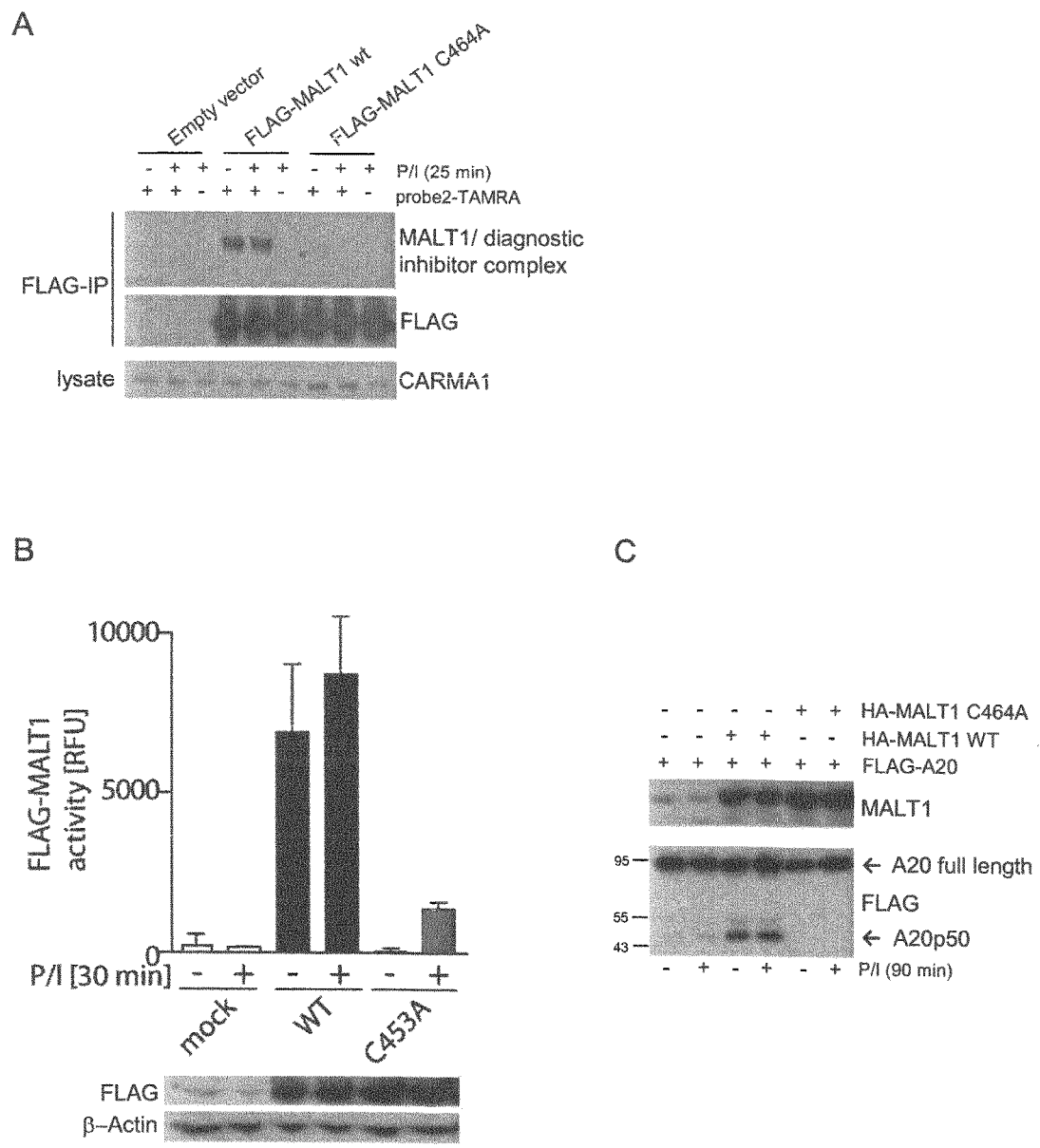
FIG. 2: A) Diagnostic MALT1 inhibitors label active MALT1, but not a MALT1 mutant, in gel-based assays.
Jurkat T cells, transfected with active FLAG-MALT2 wt or active site mutant C464A, were stained after lysis and IP with probe 2, pre-clicked to TAMRA. Analysis was done by fluorescence staining.

Initially, we analyzed, if probe 2, pre-clicked to the fluorophore TAMRA, could be used as diagnostic inhibitor to detect irreversible active MALT1-inhibitor complexes in gel-based assays. Overexpressed FLAG-MALT1 wt but not the catalytic inactive mutant was detected by probe 2 after FLAG immunoprecipitation in Jurkat T cells (FIG. 2A). MALT1 labeling with the diagnostic inhibitor (probe 2) exactly matched the results of cleavage assays using transfected MALT1 (FIG. 2). Notably, the high concentration of overexpressed MALT1 induces dimerization and oligomerization that promotes activation even in the absence of stimulation [10, 28].

In addition, we attempted to analyze active endogenous MALT1 in T cells by using probe 5, directly coupled to a FITC fluorophore. Jurkat T cells were stimulated via TCR by anti-CD3/CD28 coligation and probe 5 labeling was performed in whole cell lysates to investigate the specificity of our compound. Endogenous active MALT1-probe 5 complexes were exclusively detected after T cell stimulation (FIG. 3A). Further, probe 5 detected active MALT1 in extracts of P/I-stimulated primary blood mononuclear cells (PBMCs) and human T cells (FIG. 3B). The data demonstrate that the diagnostic inhibitors of MALT1 of the present invention are not reacting with inactive MALT1 in unstimulated Jurkat T cells, while they can be used to detect the activated enzyme from stimulated T cells. Labeling of active MALT1 was confirmed by the reduction of MALT1 amounts upon siRNA transfection (FIG. 5) or by pre-incubating the cells with the covalent, active site MALT1 inhibitor z-VRPR-FMK (SEQ ID No. 6) or the allosteric, reversible MALT1 inhibitors mepazine and thioridazine [17, 29] (FIG. 3A).

Importantly, MALT1 was the only inducible band in extracts labeled with probe 5, although some background signals were obtained. One band below 34 kDa (see open circle) was also reduced by z-VRPR-FMK (SEQ ID No. 6), but unaffected by mepazine or thioridazine. We assumed cross-reactivity with cysteine proteases of the cathepsin family like cathepsin B, which migrates at the respective size and displays a preference for arginine at the P1 position [30]. Indeed, in vitro protease activity measurements revealed that probe 5 and also z-VRPR-FMK (SEQ ID No. 6) did not only inhibit MALT1, but also abrogated cathepsin B activity even though slightly less efficient (FIG. 3C). As expected, Caspase 8 activity was not affected by the diagnostic inhibitors of MALT1 of the present invention. Further, neither the non-competitive MALT1 inhibitor mepazine, nor the irreversible cathepsin B specific inhibitor CA-074 showed any cross-inhibition of cathepsin B or MALT1, respectively. In agreement with cross-reaction of the diagnostic MALT1 inhibitors of the present invention and cathepsin B, preincubation of CA-074Me in Jurkat T cells completely abolished detection of the ~30 kDa signal while inducible MALT1 labeling was unaffected (FIG. 3D).

Thus, tetrapeptides that target the active site of MALT1 are also binding to cathepsin B. Since serine (LRSR) (SEQ ID No. 5) or proline (VRPR) (SEQ ID No. 6) at the P2 position is already poorly tolerated by cysteine cathepsins [31], improvement of the peptide scaffold may be very difficult.

Example 4: BODIPY-Detection of Active MALT1 in ABC DLBCL Cells

Figure 6:
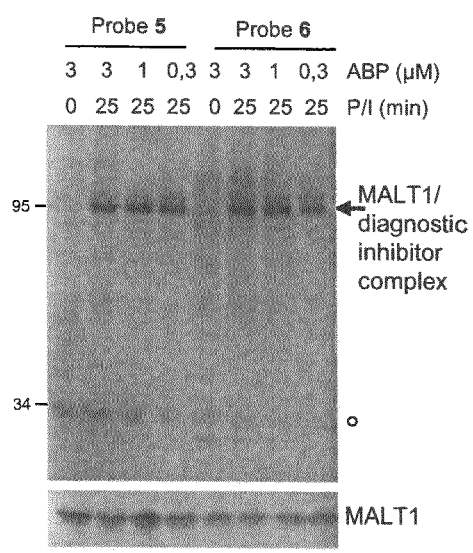

Constitutive MALT1 protease activity is a hallmark of ABC DLBCL cells and we tested, if the diagnostic inhibitors of the present invention can be used to label active MALT1 in lymphoma cells. As active MALT1 signal was not detectable in whole cell extracts labeled with probe 5, we synthesized probe 6 with the strong emitting BODIPY fluorophore to increase signal intensity [32]. Indeed, probe 6 was slightly more effective in active MALT1 labeling, while cathepsin B labeling was even reduced (FIG. 6). In extracts of ABC cell line HBL1 cells, probe 6 weakly labeled active MALT1, confirmed by the sensitivity to z-VRPR-FMK (SEQ ID No. 6) and mepazine inhibition (FIG. 3E). However, the ~30 kDa cathepsin B signal, sensitive to z-VRPR-FMK (SEQ ID No. 6) and CA-074Me but not to mepazine treatment, was highly abundant in HBL1 cells. Also other ABC DLBCL cells show enhanced signals around 30-40 kDa with probe 6, revealing putatively high activity of cathepsin-type proteases in some ABC DLBCL cell lines (FIG. 7). Therefore, a panel of ABC DLBCL and GCB DLBCL were pretreated with CA-074Me and subsequently labeled with probe 6 in whole cell lysates. In all ABC DLBCL cells the MALT1-probe 6 complex was detected even in the absence of any stimulation. In contrast, GCB DLBCL were all negative for labeling with the diagnostic inhibitor of the present invention (probe 6), which is in line with previous data that show constitutive MALT1 activity being restricted to the ABC DLBCL subtype (FIG. 3F).

Example 5: Enhancement of Detection of Active MALT1

Background and cross-reaction with cathepsin B may impede a broad application of diagnostic MALT1 inhibitor with fluorescent label in diagnostic assays. To boost signal intensity and selectivity of the assay, we developed the biotin-coupled probe 7. Probe 7 enables a separation of active MALT1 in Jurkat T cells using streptavidin coated beads. Subsequent antibody detection of bound MALT1 ensures selectivity (FIG. 4A). Indeed, MALT1-probe 7 complexes were exclusively detected in extracts of P/I stimulated Jurkat T cells. 100 nM of probe 7 was sufficient to completely remove active MALT1 from the extracts of stimulated T cells, because no residual MALT1 activity could be detected in the supernatant using the fluorescent MALT1-inhibitor probe 6 (FIG. 4A; lower panel). Most of cellular MALT1 was not pulled down in the stimulated T cells, suggesting that only a minor fraction of MALT1 gets activated (FIG. 4A).

In line with a previous report on the requirement for ubiquitination to activate MALT1 [14], precipitated MALT1-probe 7 complexes were more slowly migrating and thus represent a completely modified form of MALT1 (FIG. 4B). Formation of MALT1-probe 7 complexes can be blocked by treating the Jurkat T cells with MALT1 inhibitors z-VRPR-FMK (SEQ ID No. 6) and mepazine and could also be detected in response to CD3/CD28 co-ligation (FIGS. 4C and 4D).

To further develop probe 7 for diagnostic applications, we captured active MALT1-probe 7 complexes on streptavidin-coated plates to perform an ELISA-type of reaction in which we detect the immobilized active MALT1 by antibody staining in 96-well format. Congruent with the results after precipitation, MALT1 binding to streptavidin-coated plates was only detected in P/I or CD3/CD28 stimulated Jurkat T cells (FIG. 4E). In addition, strongly decreased signals in MALT1 inhibitor treated cells revealed, that only active MALT1 was detected in the ELISA-type affinity reaction. The high sensitivity of detection was further confirmed by showing that 10 nM or less of probe 7 was sufficient to obtain a robust increase in active MALT1 (FIG. 8). Labeling of $2 \times 10^6$ primary human T cells with the BODIPY probe 6 revealed a weak active MALT1 signal (FIG. 4F; right panel), demonstrating that the gel-based assay reached its detection limit. In contrast, using the sensitive ELISA, a robust induction of active MALT1 in stimulated primary T cells was observed (FIG. 4F; left panel). We asked whether biotinylated probe 7 could be a reliable tool to measure constitutive MALT1 activity in lymphoma cell lines and to discriminate between ABC and GCB DLBCL cells. Indeed, after streptavidin pulldown and subsequent Western Blot, we detected constitutively active MALT1 exclusively in ABC, but not in GCB DLBCL cells (FIG. 4G). Again, the active MALT1 activity assay revealed a significant increase in MALT1 activity in ABC DLBCL cells when compared to GCB DLBCL cells. The signal was strongly reduced by MALT1 inhibitors z-VRPR-FMK (SEQ ID No. 6) and mepazine, but the signal was resistant to the cathepsin B inhibitor CA-074Me, proofing the selectivity and specificity of MALT1 detection (FIG. 4H).

In conclusion, we generated four different diagnostic inhibitors for activated MALT1 as novel chemical tools for detection of active MALT1 in lymphocytes and lymphoma cells. We provide evidence that tetrapeptide recognition is not sufficient to discriminate between MALT1 and cathepsin B activity and therefore we established a highly sensitive sandwich based ELISA system, that can be transferred to a fast and easy to handle diagnostic test. To our knowledge, this is the first description of an ELISA-type test for monitoring activity of a cellular cysteine protease. Given the impact of MALT1 proteolytic activity in autoimmune diseases and subtypes of malignant lymphomas, the diagnostic MALT1 inhibitors of the present invention will facilitate the diagnosis of patients that benefit from MALT1-directed therapy. Further, the diagnostic MALT1 inhibitor of the present invention will help to monitor efficacy of small molecule MALT1 inhibition in patient samples in response to therapy.

Example 6: Monitoring Cellular MALT1 Inhibition by Small Molecules

In addition, we tested if the "MALT1 ELASA" (the term "MALT1 ELASA" is an acronym for the plate-bound MALT1 Enzyme Linked Activity Sorbent Assay) could be used for cellular inhibitor profiling and treated the ABC DLBCL cell line OCI-Ly3 with increasing concentrations of the allosteric MALT1 inhibitor (S-)mepazine or the irreversible MALT1 inhibitor MI-2 [23, 29] (FIG. 9A). Both compounds inhibited cellular MALT1 at similar concentrations with S-mepazine being slightly more potent.

Also combinatorial studies of inhibitors S-mepazine and ibrutinib in ABC DLBCL cell lines were performed in comparison to single inhibitor treatment (FIG. 9B). A single treatment with increasing concentrations of Ibrutinib (0.3-10 nM) for 18 h reduced MALT1 activity in a dose dependent manner in CD79 mutant cells HBL1, OCI-Ly10 and TMD8 cells. However, MALT1 activity was not affected in CARMA1 mutant OCI-Ly3 cells. In contrast, the allosteric MALT1 inhibitor S-mepazine inhibited MALT1 in all ABC DLBCL cell lines at concentrations between 0.3-10 µM. To test combinatorial effects, we incubated the cells with 0.5 nM ibrutinib to achieve approximately 50-60% reduction of MALT1 activity and added increasing concentrations of S-mepazine (FIG. 1C). Combinatorial treatment of ibrutinib and S-mepazine augmented MALT1 inhibition and resulted in a more severe reduction of MALT1 activity when compared to single agent treatment in ibrutinib responsive ABC DLBCL cells, but not in ibrutinib resistant OCI-Ly3 cells. The analysis revealed additive effects of combinatorial treatments. Thus, the ELASA represents a fast and reliable assay to measure effects of compounds on MALT1 activity for drug discovery.

Example 7: Patient Biopsies and Oncogenic Status

We wanted to address if the ELASA could be used to detect active MALT1 in a clinically relevant diagnostic-type of setting. For this, we evaluated whether active MALT1 can be detected in cryo-preserved primary lymphoma tissue from 15 DLBCL tumor patients that have been classified as ABC DLBCL (8 biopsies) or GCB DLBCL (7 biopsies) by gene expression profiling. Cryo-sections were directly lysed yielding between 200-560 µg total protein amount for each biopsy. Samples were split in half and either left untreated or incubated with z-VRPR-FMK (SEQ ID No. 6) before ELASA (FIG. 10A). In general, due to limited material the relative MALT1 activities were low in all DLBCL samples. As the number of tumor cells and absolute protein amounts from individual tumor tissue varies, we compared MALT1 activity in the untreated samples to z-VRPR-FMK (SEQ ID No. 6) inhibited samples. Z—VRPR-FMK (SEQ ID No. 6) treatment led to reduction in MALT1 activity in five out of eight ABC DLBCL samples, but only in one out of seven GCB DLBCL samples, suggesting that MALT1 activity is indeed more often found in ABC DLBCL tumors. Congruently, there was a significant reduction of MALT1 activity only in the subset of z-VRPR-FMK (SEQ ID No. 6) treated ABC, but not the GCB DLBCL samples (FIG. 10A). However, we also observed considerable heterogeneity in MALT1 activity also within the two DLBCL sub-entities, because not all ABC DLBCL samples responded to inhibitor treatment and also one GCB DLBCL showed inhibition. In fact, oncogenic lesions in BCR upstream regulators like CD79B and CARMA1 are not confined to ABC DLBCL [34-36], suggesting that MALT1 may also be active in some GCB DLBCL tumors. To test if expression of oncogenic mutations derived from the different sub-entities is sufficient to activate MALT1, we expressed CARMA1 WT, and the oncogenic mutations L244P (ABC derived) and L225LI (GCB derived) in the GCB DLBCL cell line BJAB (FIG. 10B). Whereas CARMA1 WT failed to induce MALT1 activity, both oncogenic lesions independent of their DLBCL origin were enhancing MALT1 activity. Thus, our data reveal that the MALT1 chemical probes in combination with the ELASA can be used to detect enhanced MALT1 activity in primary cancer patient biopsies.

Example 8: Active MALT1 Labeling with the Fluorescent Pentapeptide Probe BODIPY-ALVSR-AOMK (SEQ ID No. 11)

In addition to our studies with tetrapeptide (LRSR) (SEQ ID No. 5) probes, we also synthesized and tested a pentapeptide probe, which comprises the MALT1 recognition sequence found in the protein RelB [12]. The probe BODIPY-ALVSR-AOMK (SEQ ID No. 11) was synthesized according to the previously described procedures (FIG. 11A). Again, we tested if the fluorescence probe can be used to detect active endogenous MALT1 in gel-based assays. Jurkat T cells were stimulated, lysed and incubated with the fluorescent pentapeptide probe. Induced MALT1 activity can be exclusively detected after stimulation with BODIPY-ALVSR-AOMK (SEQ ID No. 11). We observed unspecific background labeling of unknown identity at approx. 40 kDa (FIG. 11B). By titrating probe concentration, we could decrease background labeling, while active MALT1 activity stays stable (FIG. 11C). Thus it can be concluded that alternative recognition elements like LVSR (SEQ ID No. 7) as well as longer pentapeptide probes can also be used for active MALT1 detection in assays as described above. The different amino acid sequence can further improve probe properties, including effectivity, selectivity, stability and cell permeability.

CITED PRIOR ART

[1] B. F. Cravatt, A. T. Wright, J. W. Kozarich, *Annu Rev Biochem* 2008, 77, 383.
[2] W. P. Heal, T. H. Dang, E. W. Tate, *Chem Soc Rev* 2011, 40, 246.
[3] S. Serim, U. Haedke, S. H. Verhelst, *ChemMedChem* 2012, 7, 1146.
[4] R. Rahal, M. Frick, R. Romero, J. M. Korn, R. Kridel, F. Chun Chan, B. Meissner, H. E. Bhang, D. Ruddy, Kauffmann A, Farsidjani A, Derti A, Rakiec D, Naylor T, Pfister E, Kovats S, Kim S, Dietze K, Dörken B, Steidl C, Tzankov A, Hummel M, Monahan J, Morrissey M P, Fritsch C, Sellers W R, Cooke V G, Gascoyne R D, Lenz G, Stegmeier F. *Nat Med* 2014, 20, 87.
[5] E D Remstein, C D James & P J Kurtin, *Am J Pathol* 2000, 156, 1183.
[6] M. Vincendeau, D. Nagel, A. C. Eitelhuber & D. Krappmann, *Int J Hematol Oncol* 2013, 2, 409.
[7] E. M. Murga Penas, H. Kawadler, R. Siebert, M. Frank, H. Ye, K. Hinz, C. Becher, M. Hummel, T. F. Barth, C. Bokemeyer, H. Stein, L. Trümper, P. Möller, P. Marynen, M Q Du, X. Yang, M. L. Hansmann, J. Dierlamm *Genes Chromosomes Cancer* 2006, 45, 863.
[8] G. Blum, S. R. Mullins, K. Keren, M. Fonovic, C. Jedeszko, M. J. Rice, B. F. Sloane, M. Bogyo, *Nat Chem Biol* 2005, 1, 203.
[9] D. Greenbaum, A. Baruch, L. Hayrapetian, Z. Darula, A. Burlingame, K. F. Medzihradszky, M. Bogyo, *Mol Cell Proteomics* 2002, 1, 60.
[10] C. Wiesmann, L. Leder, J. Blank, A. Bernardi, S. Melkko, A. Decock, A. D'Arcy, F. Villard, P. Erbel, N. Hughes, F. Freuler, R. Nikolay, J. Alves, F. Bornancin, M. Renatus, *J Mol Biol* 2012, 419, 4.
[11] J. W. Yu, P. D. Jeffrey, J. Y. Ha, X. Yang, Y. Shi, *Proc Natl Acad Sci USA* 2011, 108, 21004.
[12] J. Hachmann, S. J. Snipas, B. J. van Raam, E. M. Camino, E. J. Houlihan, M. Poreba, P. Kasperkiewicz, M. Drag, G. S. Salvesen, *Biochem J* 2012, 443, 287.
[13] A. G. Uren, K. O'Rourke, L. A. Aravind, M. T. Pisabarro, S. Seshagiri, E. V. Koonin, V. M. Dixit, *Mol Cell* 2000, 6, 961.
[14] C. Pelzer, K. Cabalzar, A. Wolf, M. Gonzalez, G. Lenz, M. Thome, *Nat Immunol* 2013, 14, 337.
[15] B. Coornaert, M. Baens, K. Heyninck, T. Bekaert, M. Haegman, J. Staal, L. Sun, Z. J. Chen, P. Marynen, R. Beyaert, *Nat Immunol* 2008, 9, 263.
[16] M. Duwel, V. Welteke, A. Oeckinghaus, M. Baens, B. Kloo, U. Ferch, B. G. Darnay, J. Ruland, P. Marynen, D. Krappmann, *J Immunol* 2009, 182, 7718.
[17] F. Rebeaud, S. Hailfinger, A. Posevitz-Fejfar, M. Tapernoux, R. Moser, D. Rueda, O. Gaide, M. Guzzardi, E. M. Iancu, N. Rufer, N. Fasel, M. Thome, *Nat Immunol* 2008, 9, 272.
[18] A. Brustle, D. Brenner, C. B. Knobbe, P. A. Lang, C. Virtanen, B. M. Hershenfield, C. Reardon, S. M. Lacher, J. Ruland, P. S. Ohashi, T. W. Mak, *J Clin Invest* 2012, 122, 4698.
[19] C. Mc Guire, P. Wieghofer, L. Elton, D. Muylaert, M. Prinz, R. Beyaert, G. van Loo, *J Immunol,* 190 2013, 2896.
[20] U. Ferch, B. Kloo, A. Gewies, V. Pfander, M. Duwel, C. Peschel, D. Krappmann, J. Ruland, *J Exp Med* 2009, 206, 2313.
[21] S. Hailfinger, G. Lenz, V. Ngo, A. Posvitz-Fejfar, F. Rebeaud, M. Guzzardi, E. M. Penas, J. Dierlamm, W. C. Chan, L. M. Staudt, M. Thome, *Proc Natl Acad Sci USA* 2009, 106, 19946.
[22] S. Rosebeck, L. Madden, X. Jin, S. Gu, I. J. Apel, A. Appert, R. A. Hamoudi, H. Noels, X. Sagaert, P. Van Loo, M. Baens, M. Q. Du, P. C. Lucas, L. M. McAllister-Lucas, *Science* 2011, 331, 468.
[23] L. Fontan, C. Yang, V. Kabaleeswaran, L. Volpon, M. J. Osborne, E. Beltran, M. Garcia, L. Cerchietti, R. Shaknovich, S. N. Yang, F. Fang, R. D. Gascoyne, J. A. Martinez-Climent, J. F. Glickman, K. Borden, H. Wu, A. Melnick, *Cancer Cell* 2012, 22, 812.
[24] D. Nagel, S. Spranger, M. Vincendeau, M. Grau, S. Raffegerst, B. Kloo, D. Hlahla, M. Neuenschwander, J. Peter von Kries, K. Hadian, B. Dorken, P. Lenz, G. Lenz, D. J. Schendel, D. Krappmann, *Cancer Cell* 2012, 22, 825.
[25] J. Staal, Y. Driege, T. Bekaert, A. Demeyer, D. Muyllaert, P. Van Damme, K. Gevaert, R. Beyaert, *EMBO J* 2011, 30, 1742.
[26] D. Kato, K. M. Boatright, A. B. Berger, T. Nazif, G. Blum, C. Ryan, K. A. Chehade, G. S. Salvesen, M. Bogyo, *Nat Chem Biol* 2005, 1, 33.
[27] A. E. Speers, G. C. Adam, B. F. Cravatt, *J Am Chem Soc* 2003, 125, 4686.
[28] Q. Qiao, C. Yang, C. Zheng, L. Fontan, L. David, X. Yu, C. Bracken, M. Rosen, A. Melnick, E. H. Egelman, H. Wu, *Mol Cell* 2013, 51, 766.
[29] F. Schlauderer, K. Lammens, D. Nagel, M. Vincendeau, A. C. Eitelhuber, S. H. Verhelst, D. Kling, A. Chrusciel, J. Ruland, D. Krappmann, K. P. Hopfner, *Angew Chem Int Ed Engl* 2013, 52, 10384.
[30] Y. Choe, F. Leonetti, D. C. Greenbaum, F. Lecaille, M. Bogyo, D. Bromme, J. A. Ellman, C. S. Craik, *J Biol Chem* 2006, 281, 12824.
[31] D. C. Greenbaum, W. D. Arnold, F. Lu, L. Hayrapetian, A. Baruch, J. Krumrine, S. Toba, K. Chehade, D. Bromme, I. D. Kuntz, M. Bogyo, *Chem Biol* 2002, 9, 1085.
[32] A. C. Benniston, G. Copley, *Phys Chem Chem Phys* 2009, 11, 4124.
[33] M. Ueki, M. Amemiya, Tetrahedron Letters 1987, 28, 6617.
[34] Compagno, M., Lim, W. K., Grunn, A., Nandula, S. V., Brahmachary, M., Shen, Q., Bertoni, F., Ponzoni, M., Scandurra, M., Califano, A., et al. (2009). Mutations of multiple genes cause deregulation of NF-kappaB in diffuse large B-cell lymphoma. Nature 459, 717-721.

[35] Davis, R. E., Ngo, V. N., Lenz, G., Tolar, P., Young, R. M., Romesser, P. B., Kohlhammer, H., Lamy, L., Zhao, H., Yang, Y., et al. (2010). Chronic active B-cell-receptor signalling in diffuse large B-cell lymphoma. Nature 463, 88-92.

[36] Lenz, G., Davis, R. E., Ngo, V. N., Lam, L., George, T. C., Wright, G. W., Dave, S. S., Zhao, H., Xu, W., Rosenwald, A., et al. (2008). Oncogenic CARD11 mutations in human diffuse large B cell lymphoma. Science 319, 1676-1679.

The invention claimed is:

1. A method for the detection of activated Mucosa-associated lymphoid tissue lymphoma translocation protein 1 (MALT1) in a test sample comprising the steps of:
   (a) contacting a test sample with a diagnostic inhibitor of MALT1 activity under conditions allowing the formation of a MALT1 complex of said diagnostic inhibitor and activated MALT1; and
   (b) detecting the MALT1 complex qualitatively and/or quantitatively by a first detection agent which binds to a first binding site on the MALT1 complex of (a),
   wherein said diagnostic inhibitor comprises the following covalently linked subunits:
   (i) a first subunit comprising at least one detectable label,
   (ii) a second subunit, wherein the second subunit is a tetrapeptide selected from the group consisting of LRSR (SEQ ID NO: 5), LVSR (SEQ ID NO: 7), FMSR (SEQ ID NO: 8), CLSR (SEQ ID NO: 9), GASR (SEQ ID NO: 10) or a pentapeptide comprising any of the tetrapeptides LRSR (SEQ ID NO: 5), LVSR (SEQ ID NO: 7), FMSR (SEQ ID NO: 8), CLSR (SEQ ID NO: 9) or GASR (SEQ ID NO: 10), capable of binding to the catalytic center of activated MALT1, and
   (iii) a third subunit comprising at least one moiety for linking the diagnostic inhibitor to activated MALT1, wherein the third subunit comprises AOMK wherein AOMK comprises a 2,6-dimethylphenyl group;
   wherein the first binding site is located on the diagnostic inhibitor; and
   wherein the method comprises qualitative and/or quantitative detection of activated MALT1 or the MALT1 complex by a second detection agent.

2. The method of claim 1, wherein the second detection agent binds to a second binding site on the MALT1 complex.

3. The method of claim 2, wherein the second detection agent comprises a MALT1 antibody or an antigen binding fragment of said antibody and a detectable label.

4. The method of claim 3, wherein the detectable label of the second detection agent is coupled to the MALT1 antibody or to an antibody which is capable of binding to said MALT1 antibody.

5. The method of claim 1, wherein the first detection agent is linked to a solid support.

6. The method of claim 1, wherein the first subunit of the diagnostic MALT1 inhibitor is or comprises a detectable label selected from the group consisting of biotin, glutathione, peptide comprising at least 6 histidines, glycosylated peptide, metalloprotein, metal, $Co^{2+}$, $Ni^{2+}$, $Cu^{2+}$, and $Zn^{2+}$, chromophore, fluorophore, radioisotope, Iodine125 and affinity tag.

7. The method of claim 1, wherein the first detection agent is selected from the group consisting of avidin, streptavidin, StrepTactin, HA, FLAG, GST or a functional fragment of GST, a peptide comprising at least 6 histidines, lectin and an antibody capable of binding to the detectable label.

8. The method of claim 1, wherein the second subunit of the diagnostic inhibitor is a tetrapeptide.

9. The method of claim 1, wherein the second subunit of the diagnostic inhibitor is a pentapeptide.

10. A method wherein said method is for detecting or diagnosing a disease or a predisposition for developing a disease, said disease being characterized by an increased amount of MALT1 or by an increased MALT1 activity, said method comprising the steps of:
    (a) detecting qualitatively and/or quantitatively, activated MALT1 of a test sample and of a reference sample by performing the method of claim 1;
    (b) comparing the amount of activated MALT1 in the test and the reference sample; and
    (c) concluding from the observation of an increased amount of activated MALT1 in the test sample in comparison to the reference sample that the subject from which the test sample originates is affected from the disease or has a predisposition for the disease.

11. The method of claim 10, wherein the disease is a tumor or cancer, an autoimmune disease or an inflammatory disease, selected from the group consisting of multiple sclerosis, rheumatoid arthritis, a lymphoma, MALT lymphoma, a diffuse large B-cell lymphoma of the subtype ABC-DLBCL and a mantle cell lymphoma.

12. A method wherein said method is for detecting the response or sensitivity of activated MALT1 to a therapeutic agent capable of inhibiting MALT1 activity, said method comprising the steps of:
    (a) detecting qualitatively and/or quantitatively, activated MALT1 of a test sample and of a reference sample by performing the method of claim 1, wherein the test sample is pre-incubated with the therapeutic agent;
    (b) comparing the amount of activated MALT1 in the test and the reference sample; and
    (c) concluding from a reduced detectable amount of activated MALT1 in the test sample that the subject is sensitive to the therapeutic agent.

13. A method wherein said method is for monitoring a subject's response to a medication for treating a disease characterized by an increased MALT1 activity, comprising the steps of:
    (a) detecting qualitatively and/or quantitatively, activated MALT1 of a test sample and of a reference sample both originating from the same subject by performing the method of claim 1, wherein the test sample is a sample obtained from the subject after treatment or after a treatment step of the subject with a therapeutic agent and the reference sample is obtained before the treatment or the treatment step of the subject with the therapeutic agent;

(b) comparing the amount of activated MALT1 in the test sample and the reference sample; and (c) concluding from a reduced detectable amount of activated MALT1 in the test sample in comparison with the reference sample whether the therapeutic agent affects a MALT1 response.

14. The method of claim 1, wherein the method comprises a synthesis of the diagnostic inhibitor and where the synthesis comprises a step wherein tetrabutylammonium fluoride is used as a base.

15. The method of claim 1, wherein the second subunit is LRSR.

16. The method of claim 1, wherein the second subunit is LRSR and wherein the AOMK comprises a 2,6-dimethylphenyl group.

* * * * *

UNITED STATES PATENT AND TRADEMARK OFFICE
CERTIFICATE OF CORRECTION

PATENT NO. : 10,502,741 B2
APPLICATION NO. : 15/108655
DATED : December 10, 2019
INVENTOR(S) : Daniel Krappmann et al.

Page 1 of 1

It is certified that error appears in the above-identified patent and that said Letters Patent is hereby corrected as shown below:

On the Title Page

Item (73) Assignees, replace "Umweld" with --Umwelt--;

In the Claims

Column 50, Line 25 (Claim 10), delete "wherein said method is";

Column 50, Line 46 (Claim 12), delete "wherein said method is";

Column 50, Line 59 (Claim 13), delete "wherein said method is".

Signed and Sealed this
Ninth Day of June, 2020

Andrei Iancu
*Director of the United States Patent and Trademark Office*